US010273269B2

(12) United States Patent
Ciaramella

(10) Patent No.: US 10,273,269 B2
(45) Date of Patent: Apr. 30, 2019

(54) HIGH POTENCY IMMUNOGENIC ZIKA VIRUS COMPOSITIONS

(71) Applicant: ModernaTX, Inc., Cambridge, MA (US)

(72) Inventor: Giuseppe Ciaramella, Sudbury, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 16/031,951

(22) Filed: Jul. 10, 2018

(65) Prior Publication Data

US 2018/0312549 A1 Nov. 1, 2018

Related U.S. Application Data

(63) Continuation of application No. PCT/US2018/000026, filed on Feb. 16, 2018.

(60) Provisional application No. 62/459,763, filed on Feb. 16, 2017.

(51) Int. Cl.

| | |
|---|---|
| *C07K 14/18* | (2006.01) |
| *A61P 31/14* | (2006.01) |
| *A61K 31/7105* | (2006.01) |
| *A61K 39/12* | (2006.01) |
| *A61K 39/39* | (2006.01) |
| *C07K 16/10* | (2006.01) |
| *A61K 39/00* | (2006.01) |

(52) U.S. Cl.

CPC ...... *C07K 14/1825* (2013.01); *A61K 31/7105* (2013.01); *A61K 39/12* (2013.01); *A61K 39/39* (2013.01); *A61P 31/14* (2018.01); *C07K 16/1081* (2013.01); *A61K 2039/55555* (2013.01); *C12N 2770/24123* (2013.01); *C12N 2770/24134* (2013.01)

(58) Field of Classification Search

None

See application file for complete search history.

(56) References Cited

U.S. PATENT DOCUMENTS

| | | | |
|---|---|---|---|
| 3,906,092 | A | 9/1975 | Hilleman et al. |
| 6,500,419 | B1 | 12/2002 | Hone et al. |
| 6,514,948 | B1 | 2/2003 | Raz et al. |
| 7,001,890 | B1 | 2/2006 | Wagner et al. |
| 8,217,016 | B2 | 7/2012 | Hoerr et al. |
| 8,673,316 | B2 | 3/2014 | Kinney et al. |
| 8,691,961 | B1 | 4/2014 | Puffer et al. |
| 8,710,200 | B2 | 4/2014 | Schrum et al. |
| 8,734,853 | B2 | 5/2014 | Sood et al. |
| 8,754,062 | B2 | 6/2014 | de Fougerolles et al. |
| 8,822,663 | B2 | 9/2014 | Schrum et al. |
| 8,999,380 | B2 | 4/2015 | Bancel et al. |
| 9,000,141 | B2 | 4/2015 | Chang et al. |
| 9,221,891 | B2 | 12/2015 | Bancel et al. |
| 9,267,114 | B2 | 2/2016 | Yamshchikov et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,597,380 | B2 | 3/2017 | Chakraborty et al. |
| 9,868,691 | B2 | 1/2018 | Benenato et al. |
| 9,872,900 | B2 | 1/2018 | Ciaramella et al. |
| 10,064,934 | B2 | 9/2018 | Ciaramella et al. |
| 10,064,935 | B2 | 9/2018 | Ciaramella et al. |
| 2003/0092653 | A1 | 5/2003 | Kisich et al. |
| 2005/0032730 | A1 | 2/2005 | Von Der Mulbe et al. |
| 2005/0059624 | A1 | 3/2005 | Hoerr et al. |
| 2005/0250723 | A1 | 11/2005 | Hoerr et al. |
| 2006/0172003 | A1 | 8/2006 | Meers et al. |
| 2007/0280929 | A1 | 12/2007 | Hoerr et al. |
| 2008/0025944 | A1 | 1/2008 | Hoerr et al. |
| 2008/0171711 | A1 | 7/2008 | Hoerr et al. |
| 2010/0203076 | A1 | 8/2010 | Fotin-Mleczek et al. |
| 2010/0239608 | A1 | 9/2010 | Von Der Mulbe et al. |
| 2010/0291156 | A1 | 11/2010 | Barner et al. |
| 2010/0305196 | A1 | 12/2010 | Probst et al. |
| 2011/0250225 | A1 | 10/2011 | Fotin-Mleczek et al. |
| 2011/0269950 | A1 | 11/2011 | Von Der Mulbe et al. |
| 2012/0009221 | A1 | 1/2012 | Hoerr et al. |
| 2012/0219573 | A1 | 8/2012 | Baumhof et al. |
| 2013/0022538 | A1 | 1/2013 | Rossi |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |

(Continued)

FOREIGN PATENT DOCUMENTS

| | | |
|---|---|---|
| CA | 2473135 | 6/2003 |
| EP | 1026253 | 8/2000 |

(Continued)

OTHER PUBLICATIONS

Agadjanyan et al., The Journal of Immunology, 2005, 174:1580-1586. (Year: 2005).*
Rosa et al., Immunology Letters, 2004, 92:259-268. (Year: 2004).*
U.S. Appl. No. 15/239,613, filed Aug. 17, 2016, Laska et al.
U.S. Appl. No. 16/036,318, filed Jul. 16, 2018, Ciaramella et al.
U.S. Appl. No. 16/048,154, filed Jul. 27, 2018, Ciaramella et al.

(Continued)

*Primary Examiner* — Nicole Kinsey White

(74) *Attorney, Agent, or Firm* — Wolf, Greenfield & Sacks, P.C.

(57) ABSTRACT

Provided herein, in some embodiments, are Zika Virus immunogenic compositions that include a cationic lipid nanoparticle (LNP) encapsulating messenger ribonucleic acid (mRNA) having an open reading frame encoding Zika Virus antigens, a pan HLA DR-binding epitope (PADRE), and a 5' terminal cap modified to increase mRNA translation efficiency.

28 Claims, No Drawings

Specification includes a Sequence Listing.

(56) References Cited

U.S. PATENT DOCUMENTS

| | | |
|---|---|---|
| 2013/0156849 A1 | 6/2013 | de Fougerolles et al. |
| 2013/0195867 A1 | 8/2013 | Hoerr et al. |
| 2013/0195967 A1 | 8/2013 | Guild et al. |
| 2013/0195969 A1 | 8/2013 | Geall et al. |
| 2013/0202684 A1 | 8/2013 | Geall et al. |
| 2013/0243848 A1 | 9/2013 | Lobovkina et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0037660 A1 | 2/2014 | Folin-Mleczek et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0271829 A1 | 9/2014 | Lilja et al. |
| 2014/0378538 A1 | 12/2014 | Bancel |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024141 A1 | 1/2016 | Issa et al. |
| 2016/0038612 A1 | 2/2016 | Hoge et al. |
| 2016/0317647 A1 | 11/2016 | Ciaramella et al. |
| 2016/0367658 A1 | 12/2016 | Kinney et al. |
| 2017/0065675 A1 | 3/2017 | Bancel et al. |
| 2017/0130255 A1 | 5/2017 | Wang et al. |
| 2017/0340724 A1 | 11/2017 | Ciaramella et al. |
| 2018/0002393 A1 | 1/2018 | Bancel et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |

FOREIGN PATENT DOCUMENTS

| | | |
|---|---|---|
| EP | 1083232 | 2/2005 |
| EP | 1905844 A2 | 2/2008 |
| EP | 2548960 A1 | 1/2013 |
| WO | WO 1987/005326 A1 | 9/1987 |
| WO | WO 1990/11092 | 10/1990 |
| WO | WO 1993/14778 | 8/1993 |
| WO | WO 1995/24485 | 9/1995 |
| WO | WO 1995/26204 | 10/1995 |
| WO | WO 1995/33835 | 12/1995 |
| WO | WO 1999/33982 | 7/1999 |
| WO | WO 2004/058166 A2 | 7/2004 |
| WO | WO 2004/076645 A1 | 9/2004 |
| WO | WO 2005/007689 A1 | 1/2005 |
| WO | WO 2005/009346 | 2/2005 |
| WO | WO 2006/056027 A1 | 6/2006 |
| WO | WO 2006/071903 | 7/2006 |
| WO | WO 2006/095259 | 9/2006 |
| WO | WO 2007/095976 A2 | 8/2007 |
| WO | WO 2008/052770 A2 | 5/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/115046 A2 | 10/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/144358 A1 | 11/2011 |
| WO | WO 2012/019630 A1 | 2/2012 |
| WO | WO 2012/019780 A1 | 2/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2013/055905 A1 | 4/2013 |
| WO | WO 2013/090186 A1 | 6/2013 |
| WO | WO 2013/102203 A1 | 7/2013 |
| WO | WO 2013/120497 A1 | 8/2013 |
| WO | WO 2013/120628 A1 | 8/2013 |
| WO | WO 2013/120629 A1 | 8/2013 |
| WO | WO 2013/185069 A1 | 12/2013 |
| WO | WO 2014/144196 A1 | 9/2014 |
| WO | WO 2014/152774 A1 | 9/2014 |
| WO | WO 2014/152940 A1 | 9/2014 |
| WO | WO 2014/160243 A1 | 10/2014 |
| WO | WO 2015/024668 A2 | 2/2015 |
| WO | WO 2015/130584 A1 | 9/2015 |
| WO | WO 2016/092460 A2 | 6/2016 |
| WO | WO 2016/116904 A1 | 7/2016 |
| WO | WO 2016/164762 A1 | 10/2016 |
| WO | WO 2016/184822 A1 | 11/2016 |
| WO | WO 2016/191641 A2 | 12/2016 |
| WO | WO 2016/201377 A1 | 12/2016 |
| WO | WO 2017/015457 A1 | 1/2017 |
| WO | WO 2017/015463 A1 | 1/2017 |
| WO | WO 2017/020026 A1 | 2/2017 |
| WO | WO 2017/021546 A1 | 2/2017 |
| WO | WO 2017/062513 A1 | 4/2017 |
| WO | WO 2017/070601 A1 | 4/2017 |
| WO | WO 2017/070616 A1 | 4/2017 |
| WO | WO 2017/070618 A1 | 4/2017 |
| WO | WO 2017/070620 A1 | 4/2017 |
| WO | WO 2017/070623 A1 | 4/2017 |
| WO | WO 2017/070624 A1 | 4/2017 |
| WO | WO 2017/083963 A1 | 5/2017 |
| WO | WO 2017/109222 | 6/2017 |
| WO | WO 2017/140905 A1 | 8/2017 |
| WO | WO 2017/147458 | 8/2017 |
| WO | WO 2017/165317 | 9/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/208191 | * 12/2017 |
| WO | WO 2017/208191 A1 | 12/2017 |
| WO | WO 2017/210215 | 12/2017 |
| WO | WO 2018/020271 A1 | 2/2018 |
| WO | WO 2018/052549 | 3/2018 |
| WO | WO 2018/053209 A1 | 3/2018 |
| WO | WO 2018/075980 A1 | 4/2018 |
| WO | WO 2018/081459 A1 | 5/2018 |
| WO | WO 2018/089851 A1 | 5/2018 |
| WO | WO 2018/091540 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |

OTHER PUBLICATIONS

U.S. Appl. No. 16/144,394, filed Sep. 27, 2018, Ciaramella et al.
U.S. Appl. No. 90/014,167, filed Aug. 17, 2018, Ciaramella et al.
U.S. Appl. No. 15/748,773, filed Jan. 30, 2018, Ciaramella et al.
U.S. Appl. No. 15/155,986, filed May 16, 2016, Fritz.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 16/001,751, filed Jun. 6, 2018, Mousavi et al.
U.S. Appl. No. 15/156,249, filed May 16, 2016, Miracco.
U.S. Appl. No. 15/767,587, filed Apr. 11, 2018, Ciaramella.

(56) References Cited

OTHER PUBLICATIONS

U.S. Appl. No. 16/006,526, filed Jun. 12, 2018, Ciaramella.
U.S. Appl. No. 15/767,600, filed Apr. 11, 2018, Ciaramella et al.
U.S. Appl. No. 16/023,013, filed Jun. 29, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 15/674,585, filed Aug. 11, 2017, Ciaramella et al.
U.S. Appl. No. 16/136,386, filed Sep. 20, 2018, Ciaramella et al.
U.S. Appl. No. 15/674,591, filed Aug. 11, 2017, Ciaramella et al.
U.S. Appl. No. 16/136,503, filed Sep. 20, 2018, Ciaramella et al.
U.S. Appl. No. 15/746,286, filed Jan. 19, 2018, Ciaramella et al.
U.S. Appl. No. 16/009,811, filed Jun. 15, 2018, Ciaramella et al.
U.S. Appl. No. 16/009,848, filed Jun. 15, 2018, Ciaramella et al.
U.S. Appl. No. 16/009,880, filed Jun. 15, 2018, Ciaramella et al.
U.S. Appl. No. 15/981,762, filed May 16, 2018, Bancel et al.
U.S. Appl. No. 15/905,576, filed Feb. 26, 2018, Bancel et al.
U.S. Appl. No. 15/387,263, filed Dec. 21, 2016, Chen et al.
U.S. Appl. No. 15/674,107, filed Aug. 10, 2017, Besin et al.
U.S. Appl. No. 15/674,872, filed Aug. 11, 2017, Besin et al.
U.S. Appl. No. 16/001,786, filed Jun. 6, 2018, Hoge et al.
U.S. Appl. No. 16/040,981, filed Jul. 20, 2018, Ciaramella et al.
U.S. Appl. No. 16/001,765, filed Jun. 6, 2018, Marquardt et al.
U.S. Appl. No. 16/025,302, filed Jul. 2, 2018, Ticho et al.
U.S. Appl. No. 15/880,436, filed Jan. 25, 2018, Ciaramella.
U.S. Appl. No. 16/131,793, filed Sep. 14, 2018, Ciaramella et al.
PCT/US2018/000026, May 3, 2018, International Search Report and Written Opinion.
[No Author Listed], "Messenger RNA", Internet: Wikipedia. Jun. 19, 2013, XP002699196, Retrieved from the Internet: URL: http://en.wikipedia.org/wiki/Messenger RNA.
Agadjanyan, Prototype Alzheimer's Disease Vaccine Using the Immunodominant B Cell Type from Beta-Amyloid and Promiscuous T Cell Epitope Pan HLA DR-Binding Peptide. J Immunol. Feb. 1, 2005;174(3):1580-6.
Archer, Induction of a T-cell specific antigen on bone marrow lymphocytes with thymus RNA. Immunology. Jan. 1978;34(1):123-9.
Ashley et al., Bone marrow-generated dendritic cells pulsed with tumor extracts or tumor RNA induce antitumor immunity against central nervous system tumors. J Exp Med. Oct. 6, 1997; 186(7): 1177-82.
Bettinger et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill et al., Single-step antigen loading and activation of dendritic cells by mRNA electroporation for the purpose of therapeutic vaccination in melanoma patients. Clin Cancer Res. May 2009; 15(10): 3366-3375.
Conry et al., Characterization of a messenger RNA polynucleotide vaccine vector. Cancer Res. Apr. 1, 1995 ;55 (7):1397-1400.
Dahlman et al., in vivo endothelial siRNA delivery using polymeric nanoparticles with low molecular weight, Nature Nanotechnology, 2014, No vol. #, pp. 1-8.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
GenBank Accession No. KJ776791, first seen on NCBI on May 12, 2014.
Gilboa et al., Cancer immunotherapy with mRNA-transfected dendritic cells. Immunol Rev. Jun. 2004;199:251-63.
Hecker et al., Non-Viral DNA and mRNA Gene Delivery to the CNS Pre-Operatively for Neuroprotection and Following Neurotrauma. Molecular Therapy. 2004; 9, S258-S258.
Heiser et al., Induction of polyclonal prostate cancer-specific CTL using dendritic cells transfected with amplified tumor RNA. J Immunol. Mar. 1, 2001; 166(5):2953-60.
Heyes et al., Cationic lipid saturation influences intracellular delivery of encapsulated nucleic acids. J Control Release. Oct. 3, 2005;107(2):276-87.
Hoerr et al., In vivo application of RNA leads to induction of specific cytotoxic T lymphocytes and antibodies. EurJ Immunol. Jan. 2000;30(1):1-7.
Hoerr et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp et al., Modification of antigen-encoding RNA increases stability, translational efficacy, and T-cell stimulatory capacity of dendritic cells. Blood. Dec. 15, 2006;108(13):4009-17.
Hung et al., DNA vaccines encoding Ii-PADRE generates potent PADRE-specific CD4+ T-cell immune responses and enhances vaccine potency. Mol Ther. Jun. 2007;15(6):1211-9. Epub Mar. 13, 2007.
Jirikowski et al., Reversal of diabetes insipidus in Brattleboro Rats: Intrahypothalamic injection of vasopressin mRNA. Science. Feb. 1992; 255(5047): 996-998.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kisich et al., Antimycobacterial agent based on mRNA encoding human beta-defensin 2 enables primary macrophages to restrict growth of *Mycobacterium tuberculosis*.Infect Immun Apr. 2001;69(4):2692-9.
Kozielski et al., Bioreducible Cationic Polymer-Based Nanoparticles for Efficient and Environmentally Triggered Cytoplasmic siRNA Delivery to Primary Human Brain Cancer Cells, ACS Nano. Apr. 22, 2014;8(4):3232-41. doi: 10.1021/nn500704t. Epub Apr. 3, 2014.
Kreiter et al., Intranodal vaccination with naked antigen-encoding RNA elicits potent prophylactic and therapeutic antitumoral immunity. Cancer Res. 2010; 70: 9031-9040.
Kreiter et al., Tumor vaccination using messenger RNA: prospects of a future therapy. Curr Opinion in Immun. Jun. 2011; 23(3): 399-406.
Kuhn et al., mRNA as a versatile tool for exogenous protein expression. Current Gene Therapy. Oct. 2012; 12 (5): 347-361.
Leitner et al., DNA and RNA-based vaccines: principles, progress and prospects. Vaccine. Dec. 10, 1999;18 (9-10):765-77.

(56) References Cited

OTHER PUBLICATIONS

Li et al., Overcoming obstacles to develop effective and safe siRNA therapeutics. Expert Opin Biol Ther. May 2009; 9(5): 609-19.
Lorenzi et al., Intranasal vaccination with messenger RNA as a new approach in gene therapy: Use against tuberculosis. BMC Biotechnol. Oct. 2010; 10(77): 1-11.
Mackey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Madden et al., Administration of nucleoside-modified mRNA encoding broadly neutralizing antibody protects humanized mice from HIV-1 challenge. Nat Commun. Mar. 2, 2017;8:14630. doi: 10.1038/ncomms14630. Available at haps://acuitastx.com/wp-content/uploads/2015/01/Poster-Second-International-mRNA-Health-Conference.pdf.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Martinon et al., Induction of virus-specific cytotoxic T lymphocytes in vivo by liposome-entrapped mRNA. EurJ lmmunol. Jul. 1993;23(7):1719-22.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mal Ther. Apr. 2000;2(2):176-81.
Mitchell et al., RNA-transfected dendritic cells in cancer immunotherapy. J Clin Invest. Nov. 2000;106 (9):1065-9.
Muller et al., Transfection of dendritic cells with RNA induces CD4- and COB-mediated T cell immunity against breast carcinomas and reveals the immunodominance of presented T cell epitopes. J lmmunol. Jun. 15, 2003;170 (12):5892-6.
Parisien et al., Rationalization and prediction of selective decoding of pseudouridine-modified nonsense and sense codons. RNA. Mar. 2012;18(3):355-67. doi: 10.1261/rna.031351.111. Epub Jan. 26, 2012.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pollard et al., Type I IFN counteracts the induction of antigen-specific immune responses by lipid-based delivery of mRNA vaccines. Mol Ther. Jan. 2013;21(1):251-9. doi: 10.1038/mt.2012.202. Epub Sep. 25, 2012.
Pulford et al., Liposome-siRNA-peptide complexes cross the blood-brain barrier and significantly decrease PrP'C on neuronal cells and PrP'Res in infected cell cultures. PLoS One. 201 O; 5(6): e11085, (2010).
Rabinovich, P.M., et al., Synthetic messenger RNA as a tool for gene therapy. Hum. Gene Ther. Oct. 2006; 17: 1027-1035.
Richner et al., Modified mRNA Vaccines Protect against Zika Virus Infection. Cell. Mar. 23, 2017;169(1):176. doi: 10.1016/j.cell.2017.03.016.
Richner et al., Vaccine Mediated Protection Against Zika Virus-Induced Congenital Disease. Cell. Jul. 13, 2017;170(2):273-283.e12. doi: 10.1016/j.cell.2017.06.040.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Schmitt et al., In vitro induction of a bladder cancer-specific T-cell response by mRNA-transfected dendritic cells. J Cancer Res Clin Oncol. 2001 ;127(3):203-6.
Schott et al., Viral and non-viral approaches for transient delivery of mRNA and proteins. Current Gene Ther. 2011; 11 (5): 382-398.
Segura et al., Monitoring gene therapy by external imaging of mRNA: Pilot study on murine erythropoietin. Ther Drug Monit. Oct. 2007; 29(5): 612-8.
Smits et al., RNA-based gene transfer for adult stem cells and T cells. Leukemia. 2004; 18: 1898-1902.
Sohn et al., In-vivo particle mediated delivery of mRNA to mammalian tissues: ballistic and biological effects. Wound Rep and Regen. Jul.-Aug. 2001; 287-296.
Strong et al., Incorporation of beta-globin untranslated regions into a Sindbis virus vector for augmentation of heterologous mRNA expression. Gene Ther. Jun. 1997;4(6):624-7.
Sullenger et al., Emerging clinical applications of RNA. Nature. Jul. 11, 2002;418(6894):252-8.
Tavernier et al., mRNA as gene therapeutic: How to control protein expression. J. of Controlled Release. Mar. 2011; 150(3): 238-247.
Tekmira, Lipid Nanoparticle-mediated delivery of messenger RNA (retrieved from the internet). Published Oct. 24, 2013. Available at http://files.shareholder.com/downloads/ABEA-50QJTB/2628241206x0x699789/47543d12-db34-4e6e-88a9-f3ae5d97b1d2/MacLachlan_mRNA_Conf_2013.pdf.
Teufel et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Wong et al., An mRNA vaccine for influenza. Nat Biotechnol. Dec. 2012;30(12):1202-4. doi: 10.1038/nbt.2439.
Yamamoto et al., Current prospects for mRNA gene delivery, European Journal of Pharmaceutics and Biopharmaceutics 71 (2009) 484-489.
Zhou et al., RNA melanoma vaccine: induction of antitumor immunity by human glycoprotein 100 mRNA immunization. Hum Gene Ther. Nov. 1, 1999;10(16):2719-24.

\* cited by examiner

HIGH POTENCY IMMUNOGENIC ZIKA VIRUS COMPOSITIONS

RELATED APPLICATION

This application is a continuation of international application number PCT/US2018/000026, filed Feb. 16, 2018, which claims the benefit under 35 U.S.C. § 119(e) of U.S. provisional application No. 62/459,763, filed Feb. 16, 2017, each of which is incorporated by reference herein in its entirety.

BACKGROUND

Zika virus (ZIKV) was identified in 1947 from a sentinel Rhesus monkey in the Zika Forest of Uganda. Historically, ZIKV circulated between *Aedes* species mosquitoes, non-human primates in the jungle, and episodically spilled into human populations in Africa and parts of Southeast Asia. Infection was associated with a mild, self-limiting febrile illness characterized by headache, rash, conjunctivitis, myalgia, and arthralgia. Since 2010, and especially in the context of its spread and dissemination to countries of the Western Hemisphere, more severe clinical consequences have been observed. Infection of fetuses in utero during pregnancy, particularly during the first and second trimesters, has been associated with placental insufficiency and congenital malformations including cerebral calcifications, microcephaly, and miscarriage. In adults, ZIKV infection is linked to an increased incidence of Guillain-Barré syndrome (GBS), an autoimmune disease characterized by paralysis and polyneuropathy. In addition to mosquito and in utero transmission, sexual transmission of ZIKV has been described from men-to-women, men-to-men, and women-to-men. Persistent ZIKV infection can occur, as viral RNA has been detected in semen, sperm, and vaginal secretions up to 6 months following infection. Thus, ZIKV is now a global disease with locally-acquired and travel-associated transmission through multiple routes in the Americas, Africa, and Asia. The emergence of Zika virus (ZIKV) infection has prompted a global effort to develop safe and effective vaccines.

SUMMARY

Provided herein are immunogenic compositions that include lipid nanoparticles encapsulating mRNA vaccines that enhance the CD4$^+$ T cell immune response. In some embodiments, the vaccines comprise an mRNA encoding an infectious disease antigen, such as a Zika virus (ZIKV) antigen, and an mRNA encoding an immunodominant helper CD4 T cell epitope, such as a pan HLA DR-binding epitope (PADRE). CD4$^+$ T cells play an important role in the generation of CD8$^+$ T effector and memory T-cell immune responses. The CD4$^+$ T cell immune response, and thus the corresponding antigen-specific CD8$^+$ T cell response, can be enhanced by administering in a single composition an mRNA vaccine encoding a pan HLA DR-binding epitope (PADRE).

Thus, provided herein are more potent prophylactic and therapeutic immunogenic compositions (e.g., mRNA vaccines) that induce a stronger T cell response against viral, bacterial and/or parasitic antigens, relative to current vaccine therapies.

Some aspects of the present disclosure provide an immunogenic composition, comprising a cationic lipid nanoparticle (LNP) encapsulating messenger ribonucleic acid (mRNA) having an open reading frame encoding a Zika Virus (ZIKV) prM antigen, a ZIKV E antigen, a pan HLA DR-binding epitope (PADRE), and a 5' terminal cap modified to increase mRNA translation efficiency, wherein the cationic lipid nanoparticle comprises a cationic lipid, a PEG-modified lipid, a sterol and a non-cationic lipid.

Other aspects of the present disclosure provide an immunogenic composition, comprising a cationic lipid nanoparticle (LNP) encapsulating (a) a messenger ribonucleic acid (mRNA) having an open reading frame encoding a Zika Virus (ZIKV) prM antigen, a ZIKV E antigen, and a 5' terminal cap, and (b) a mRNA having an open reading frame encoding a pan HLA DR-binding epitope (PADRE), and a 5' terminal cap, wherein the 5' terminal cap of (a) and (b) are modified to increase mRNA translation efficiency, and wherein the cationic lipid nanoparticle comprises a cationic lipid, a PEG-modified lipid, a sterol and a non-cationic lipid.

In some embodiments, the ZIKV prM antigen and the ZIKV E antigen form a fusion antigen comprising a sequence identified by SEQ ID NO: 2. In some embodiments, the ZIKV prM antigen and the ZIKV E antigen form a fusion antigen comprising a sequence identified by SEQ ID NO: 4.

In some embodiments, the ratio of mRNA encoding ZIKV antigen to mRNA encoding PADRE is 0.1:1 to 10:1. In some embodiments, the ratio of mRNA encoding ZIKV antigen to mRNA encoding PADRE is 0.1:1, 0.5:1, 1:1, 2:1, 5:1 or 10:1.

In some embodiments, the open reading frame is codon optimized.

In some embodiments, at least 80% of the uracil in the open reading frame have a chemical modification. In some embodiments, at least 90% of the uracil in the open reading frame have a chemical modification. In some embodiments, 100% of the uracil in the open reading frame have a chemical modification.

In some embodiments, the chemical modification is N1-methylpseudouridine or N1-ethylpseudouridine.

In some embodiments, the chemical modification is at the 5-position of the uracil.

In some embodiments, the 5' terminal cap is 7mG(5')ppp (5')N1mpNp.

In some embodiments, the open reading frame of the mRNA further encodes a signal sequence. In some embodiments, the signal sequence is a Japanese encephalitis prM signal sequence (MWLVSLAIVTACAGA; SEQ ID NO: 11).

In some embodiments, the cationic lipid nanoparticle comprises a molar ratio of about 20-60% cationic lipid, 0.5-15% PEG-modified lipid, 25-55% sterol, and 25% non-cationic lipid.

In some embodiments, the cationic lipid is an ionizable cationic lipid and the non-cationic lipid is a neutral lipid, and the sterol is a cholesterol.

In some embodiments, the cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate, (12Z, 15Z)-N,N-dimethyl-2-nonylhenicosa-12,15-dien-1-amine, and N,N-dimethyl-1-[(1 S,2R)-2-octylcyclopropyl]heptadecan-8-amine.

In some embodiments, the cationic lipid nanoparticle comprises a compound of Formula (I). In some embodiments, the compound is selected from Compound 3, 18, 20, 25, 26, 29, 30, 60, 108-112 and 122. In some embodiments, the compound is Compound 25.

In some embodiments, the immunogenic composition is formulated in an effective amount to induce an antigen-specific immune response. In some embodiments, the antigen-specific immune response comprises a B cell response and/or T cell response. In some embodiments, the antigen-specific immune response comprises a PADRE-specific CD4+ T cell response.

In some embodiments, the antigen-specific immune response is at least 0.1-10 times stronger than an antigen-specific immune response induced in a subject administered a control immunogenic composition without an mRNA encoding a PADRE. In some embodiments, the antigen-specific immune response is at least 0.5 times stronger than an antigen-specific immune response induced in a subject administered a control immunogenic composition without an mRNA encoding a PADRE. In some embodiments, the antigen-specific immune response is at least 2 times stronger than an antigen-specific immune response induced in a subject administered a control immunogenic composition without an mRNA encoding a PADRE. In some embodiments, the antigen-specific immune response is at least 5 times stronger than an antigen-specific immune response induced in a subject administered a control immunogenic composition without an mRNA encoding a PADRE. In some embodiments, the antigen-specific immune response is at least 10 times stronger than an antigen-specific immune response induced in a subject administered a control immunogenic composition without an mRNA encoding a PADRE.

In some embodiments, the effective amount is 5 µg-100 µg of the mRNA.

Further aspects of the present disclosure provide a method of inducing an immune response in a subject, the method comprising administering to the subject the immunogenic composition in an amount effective to produce an antigen-specific immune response in the subject.

In some embodiments, a single dose of the immunogenic composition is administered to the subject. In other embodiments, a booster dose of the immunogenic composition is administered to the subject.

In some embodiments, the efficacy of the immunogenic composition against ZIKV infection is at least 50% following administration of the booster dose of the immunogenic composition. In some embodiments, the efficacy of the immunogenic composition against ZIKV infection is at least 75% following administration of the booster dose of the immunogenic composition.

In some embodiments, the immunogenic composition immunizes the subject against ZIKV for more than 2 years.

In some embodiments, the anti-ZIKV antigen antibody titer produced in the subject is increased by at least 1 log relative to a control. In some embodiments, the anti-ZIKV antigen antibody titer produced in the subject is increased by 1-3 log relative to a control.

In some embodiments, the anti-ZIKV antigen antibody titer produced in the subject is increased at least 2 times relative to a control. In some embodiments, the anti-ZIKV antigen antibody titer produced in the subject is increased 2-10 times relative to a control.

In some embodiments, the control is the anti-ZIKV antigen antibody titer produced in a subject who has not been administered a vaccine against ZIKV; who has been administered a live attenuated vaccine or an inactivated vaccine against ZIKV; who has been administered a recombinant protein vaccine or purified protein vaccine against ZIKV; or who has been administered a VLP vaccine against ZIKV.

In some embodiments, the amount is sufficient to produce detectable levels of the antigen as measured in serum of the subject at 1-72 hours post administration.

In some embodiments, the amount is sufficient to produce a 1,000-10,000 neutralization titer produced by neutralizing antibody against the antigen as measured in serum of the subject at 1-72 hours post administration.

In some embodiments, the subject is immunocompromised.

Also provided herein are uses of the immunogenic composition in the manufacture of a medicament for use in a method of inducing an antigen specific immune response to ZIKV in a subject, the method comprising administering to the subject the immunogenic composition in an amount effective to produce an antigen specific immune response to ZIKV in the subject.

Further provided herein are pharmaceutical compositions for use in vaccination of a subject comprising an effective dose of the immunogenic composition, wherein the effective dose is sufficient to produce detectable levels of ZIKV antigen as measured in serum of the subject at 1-72 hours post administration.

Further still, provided herein are pharmaceutical compositions for use in vaccination of a subject comprising an effective dose of the immunogenic composition of any one of claims 1-30, wherein the effective dose is sufficient to produce a 1,000-10,000 neutralization titer produced by neutralizing antibody against ZIKV antigen as measured in serum of the subject at 1-72 hours post administration.

Some aspects of the present disclosure provide an immunogenic composition, comprising a cationic lipid nanoparticle (LNP) encapsulating messenger ribonucleic acid (mRNA) having an open reading frame encoding at least one antigen, a pan HLA DR-binding epitope (PADRE), and a 5' terminal cap modified to increase mRNA translation efficiency, wherein the cationic lipid nanoparticle comprises a cationic lipid, a PEG-modified lipid, a sterol and a non-cationic lipid.

Other aspects of the present disclosure provide an immunogenic composition, comprising a lipid nanoparticle (LNP) encapsulating (a) a messenger ribonucleic acid (mRNA) having an open reading frame encoding at least one antigen, and a 5' terminal cap, and (b) a mRNA having an open reading frame encoding a pan HLA DR-binding epitope (PADRE), and a 5' terminal cap, wherein the 5' terminal cap of (a) and (b) is modified to increase mRNA translation efficiency, wherein the cationic lipid nanoparticle comprises a cationic lipid, a PEG-modified lipid, a sterol and a non-cationic lipid.

In some embodiments, at least one antigen is at least one viral antigen selected from a Betacoronavirus, Chikungunya virus, Dengue virus, Ebola virus, Eastern Equine Encephalitis virus, Herpes Simplex virus, Human Cytomegalovirus, Human Metapneumovirus, Human Papillomavirus, Influenza virus, Japanese Encephalitis virus, Marburg virus, Measles, Parainfluenza virus, Respiratory Syncytial virus, Sindbis virus, Varicella Zoster virus, Venezuelan Equine Encephalitis virus, West Nile virus, Yellow Fever virus, and Zika virus antigen. In some embodiments, at least one viral antigen is at least one Zika virus antigen. In some embodiments, at least one Zika virus antigen is a premembrane (prM) protein antigen and an envelope (E) protein antigen.

In some embodiments, at least one antigen is at least one bacterial antigen selected from a *Chlamydia trachomatis* antigen, a Lyme *Borrelia* and a *Streptococcal* antigen.

In some embodiments, at least one antigen is at least one parasitic antigen selected from *Plasmodium falciparum*,

*Plasmodium vivax*, *Plasmodium ovale*, and *Plasmodium malariae*, and *Plasmodium knowlesi* antigens.

DETAILED DESCRIPTION

Provided herein, in some aspects, are immunogenic compositions that include messenger ribonucleic acid (mRNA) having an open reading frame encoding at least one antigen (e.g., an infectious disease antigen), a pan HLA DR-binding epitope (PADRE), and a 5' terminal cap modified to increase mRNA translation efficiency. In some embodiments, the antigen and the PADRE are encoded on the same mRNA molecule, while in other embodiments, the antigen and the PADRE are encoded on separate mRNA molecules.

The immunogenic compositions (e.g., mRNA vaccines), in some embodiments, are formulated in a lipid nanoparticle comprising a cationic lipid, a PEG-modified lipid, a sterol and a non-cationic lipid. In some embodiments, the non-cationic lipid is Compound 25 of Formula (I). Thus, in some embodiments, an immunogenic composition comprises a mRNA encoding an antigen (e.g., a viral, bacterial, or parasitic antigen), a mRNA encoding a PADRE sequence and is formulated in a lipid nanoparticle that comprises Compound 25 of Formula (I).

In some embodiments, the immunogenic compositions (e.g., mRNA vaccines) may be used to treat a viral, bacterial, or parasitic infection in a subject (e.g., a human subject). The immunogenic compositions, in some embodiments, may be used to induce a balanced immune response, comprising both cellular and humoral immunity, without many of the risks associated with DNA vaccination.

PADRE Sequences

The immunogenic compositions (e.g., mRNA vaccines) of the present disclosure, in some embodiments, are more potent than current immunogenic compositions due, in part, to the inclusion of an immunodominant helper CD4 T cell epitope, referred to as a PADRE (pan HLA DR-binding epitope: AKFVAAWTLKAAA (SEQ ID NO: 1)). See, e.g., Alexander J. et al. *J of Immuno.* 164(3): 1625-33, incorporated herein by reference. This epitope is a potent immunogen. T cell epitopes are presented on the surface of antigen-presenting cells by MHC molecules. T cell epitopes presented by MHC class 1 molecules are typically peptides between 8 and 11 amino acids in length and exhibiting MHC-specific sequence motifs. These antigenic peptides are derived from non-structural and structural proteins through proteolysis in the cytosolic compartment. Peptide-MHC-I complexes are then transported to the cell surface of antigen presenting cells and are recognized by CD8+ cytotoxic T lymphocytes (CTL). This interaction induces the differentiation of CTLs. Activated CTL lyse the infected cell, secrete cytokines, and proliferate. This mechanism ensures that cells infected by viruses or intracellular bacteria or cancer cells can be detected, since pathogen or cancer-specific MHC peptide complexes are displayed on the cell surface. CTL can recognize such abnormal cells and eliminate them. The genes of MHC I and II molecules are polymorphic. Each MHC allele has a distinct peptide binding motif which favors certain amino acid anchor residues at defined sequence positions.

In some embodiments, a PADRE is independently encoded by a mRNA molecule that is separate from the mRNA molecule encoding an antigen of interest (e.g., a viral, bacterial or parasitic antigen). In other embodiments, an antigen of interest and a PADRE are encoded by the same mRNA molecule.

Thus, in some embodiments, the present disclosure provides immunogenic compositions that include mRNA having an open reading frame encoding at least one antigen, a pan HLA DR-binding epitope (PADRE), and a 5' terminal cap that is modified to increase mRNA translation efficiency. In other embodiments, immunogenic compositions may include (a) a messenger ribonucleic acid (mRNA) having an open reading frame encoding at least one antigen, and a 5' terminal cap that is modified to increase mRNA translation efficiency and (b) a mRNA having an open reading frame encoding a pan HLA DR-binding epitope (PADRE), and a 5' terminal cap that is modified to increase mRNA translation efficiency.

In some embodiments, the mRNA is encapsulated in a cationic lipid nanoparticle that comprises, for example, a cationic lipid, a PEG-modified lipid, a sterol and a non-cationic lipid.

The ratio of mRNA encoding antigen (e.g., viral, bacterial, or parasitic antigen) to mRNA encoding PADRE in an immunogenic composition may vary. In some embodiments, the ratio of mRNA encoding antigen to mRNA encoding PADRE is 0.1:1 to 10:1. For example, the ratio of mRNA encoding antigen to mRNA encoding PADRE may be 0.1:1, 0.2:1, 0.3:1, 0.4:1, 0.5:1, 0.6:1, 0.7:1, 0.8:1, 0.9:1, 1:1, 2:1, 3:1, 4:1, 5:1, 6:1, 7:1, 8:1, 9:1, or 10:1.

Likewise, the ratio of antigen (e.g., viral, bacterial, or parasitic antigen) to PADRE encoding by mRNA in an immunogenic composition may vary. In some embodiments, the ratio of antigen to PADRE encoded by mRNA is 1:1 to 100:1. For example, the ratio of antigen to PADRE encoded by mRNA may be 1:1, 1:2, 1:5, 1:10, 1:20, 1:30, 1:40, 1:50, or 1:100. In some embodiments, the ratio of antigen to PADRE encoded by mRNA is 1:1 to 100:1. For example, the ratio of antigen to PADRE encoded by mRNA may be 1:1, 1:2, 1:5, 1:10, 1:20, 1:30, 1:40, 1:50, or 1:100.

Messenger RNA

"Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the mRNA encoded by a DNA identified by a particular sequence identification number may also comprise the corresponding mRNA sequence encoded by the DNA, where each "T" of the DNA sequence is substituted with "U."

Polynucleotides of the present disclosure may function as mRNA but can be distinguished from wild-type mRNA in their functional and/or structural design features, which serve to overcome existing problems of effective polypeptide expression using nucleic-acid based therapeutics.

mRNA, for example, may be transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

The basic components of an mRNA molecule typically include at least one coding region, a 5' untranslated region (UTR), a 3' UTR, a 5' cap and a poly-A tail. Both the 5'UTR and the 3'UTR are typically transcribed from genomic DNA and are elements of the premature mRNA. Characteristic structural features of mature mRNA, such as the 5'-cap and the 3'-polyA tail are usually added to the transcribed (premature) mRNA during mRNA processing.

A "5' untranslated region" (5'UTR) refers to a region of an mRNA that is directly upstream (i.e., 5') from the start codon (the first codon of an mRNA transcript translated by a ribosome) that does not encode a polypeptide. In some embodiments, mRNA encoding an antigen (e.g., viral, bacterial, or parasitic antigen) and/or a PADRE includes a 5'UTR.

A "3' untranslated region" (3'UTR) refers to a region of an mRNA that is directly downstream (i.e., 3') from the stop codon (i.e., the codon of an mRNA transcript that signals a termination of translation) that does not encode a polypeptide. In some embodiments, mRNA encoding an antigen and/or PADRE includes a 3'UTR.

An "open reading frame" is a continuous stretch of DNA beginning with a start codon (e.g., methionine (ATG)), and ending with a stop codon (e.g., TAA, TAG or TGA) and encodes a polypeptide. mRNA encoding an antigen (e.g., viral, bacterial, or parasitic antigen) and/or a PADRE includes an open reading frame.

A "5' cap" is a specially altered nucleotide on the 5' end of some mRNA transcripts. In some embodiments, mRNA encoding an antigen (e.g., viral, bacterial, or parasitic antigen) and/or a PADRE includes a 5' cap (e.g., a natural 5' cap). In some embodiments, a 5' cap may be a 5' cap analog, such as a 5' diguanosine cap, tetraphosphate cap analogs having a methylene-bis (phosphonate) moiety, cap analogs having a sulfur substitution for a non-bridging oxygen, N7-benzylated dinucleoside tetraphosphate analogs, or anti-reverse cap analogs. In some embodiments, the 5' cap is a 7mG(5')ppp(5')N1mpNp cap. In some embodiments, the 5' cap is a 7mG(5')ppp(5')N1mpN2mp cap. In some embodiments, the 5' cap analog is a 5'diguanosine cap.

A "polyA tail" or "polyadenylation signal" is a region of mRNA that is downstream, e.g., directly downstream (i.e., 3'), from the 3' UTR that contains multiple, consecutive adenosine monophosphates. In some embodiments, mRNA encoding an antigen (e.g., viral, bacterial, or parasitic antigen) and/or a PADRE includes polyA tail. The polyA sequence or polyadenylation signal generally should enhance the expression level of the encoded protein. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail comprises 50 to 250 adenosine monophosphates. In some embodiments, a polyA tail comprises up to 400 adenosine monophosphates. In a relevant biological setting (e.g., in cells, in vivo) the polyA tail functions to protect mRNA from enzymatic degradation, e.g., in the cytoplasm, and aids in transcription termination, export of the mRNA from the nucleus and translation. In some embodiments, the length of a 3'-polyA tail may be an essential element with respect to the stability of the individual mRNA.

In some embodiments, mRNA includes, as a stabilizing element, a histone stem-loop. The histone stem-loop is generally derived from histone genes, and includes an intramolecular base pairing of two neighbored partially or entirely reverse complementary sequences separated by a spacer, including (e.g., consisting of) a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides. In some embodiments, mRNA comprises a 32 kDa stem-loop binding protein (SLBP), which is associated with the histone stem-loop at the 3'-end of the histone messages in both the nucleus and the cytoplasm. Its expression level is regulated by the cell cycle; it peaks during the S-phase, when histone mRNA levels are also elevated. This SLBP protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, mRNA encoding an antigen (e.g., viral, bacterial, or parasitic antigen) and/or a PADRE includes both polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, mRNA encoding an antigen (e.g., viral, bacterial, or parasitic antigen) and/or a PADRE does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, mRNA encoding an antigen (e.g., viral, bacterial, or parasitic antigen) and/or a PADRE may or may not contain a enhancer and/or promoter sequence, which may be modified or unmodified or which may be activated or inactivated.

In some embodiments, mRNA encoding an antigen (e.g., viral, bacterial, or parasitic antigen) and/or a PADRE may have one or more AU-rich sequences removed. These sequences, sometimes referred to as AURES are destabilizing sequences found in the 3'UTR. The AURES may be removed from the mRNA. Alternatively, the AURES may remain in the mRNA.

mRNA encoding an antigen (e.g., viral, bacterial, or parasitic antigen) and/or a PADRE includes 200 to 3,000 nucleotides. For example, a mRNA may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides.

Nucleic Acids

The term "nucleic acid" includes any compound and/or substance that comprises a polymer of nucleotides (nucleotide monomer). These polymers are referred to as polynucleotides. Thus, the terms "nucleic acid" and "polynucleotide" are used interchangeably.

Nucleic acids may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs), including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA), as discussed above.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity, less than 90% sequence identity, less than 85% sequence identity, less than 80% sequence identity, or less than 75% sequence identity to a naturally-occurring or wild-type sequence (e.g., a naturally-occurring or wild-type mRNA sequence encoding a polypeptide or protein of interest (e.g., antigen)).

In some embodiments, a codon-optimized sequence shares between 65% and 85% (e.g., between about 67% and about 85%, or between about 67% and about 80%) sequence identity to a naturally-occurring sequence or a wild-type sequence (e.g., a naturally-occurring or wild-type mRNA sequence encoding a polypeptide or protein of interest (e.g., an antigen)). In some embodiments, a codon-optimized sequence shares between 65% and 75%, or about 80% sequence identity to a naturally-occurring sequence or wild-type sequence (e.g., a naturally-occurring or wild-type mRNA sequence encoding a polypeptide or protein of interest (e.g., an antigen)).

In some embodiments a codon-optimized mRNA may, for example, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. International Publication No. WO 2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

"Identity" refers to a relationship between the sequences of two or more polypeptides or polynucleotides, as determined by comparing the sequences. Identity also means the degree of sequence relatedness between two sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. Identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al. (1997). "Gapped BLAST and PSI-BLAST: a new generation of protein database search programs," *Nucleic Acids Res.* 25:3389-3402). Another popular local alignment technique is based on the Smith-Waterman algorithm (Smith, T. F. & Waterman, M. S. (1981) "Identification of common molecular subsequences." *J. Mol. Biol.* 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." *J. Mol. Biol.* 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a vaccine includes at least one RNA polynucleotide having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, the RNA vaccines may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle, it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, the RNA vaccines do not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

In some embodiments, the RNA vaccines may or may not contain an enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, the RNA vaccines may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Antigens

An "antigen" is a product of mRNA transcription that is capable of inducing an immune response in a subject (e.g., human subject). Thus, in some embodiments, an antigen is a peptide or polypeptide that induces an immune response in a subject. An antigen (antigenic polypeptide) encoded by a mRNA of the present disclosure may be naturally occurring or synthetic. An antigen may be a single molecule or may be a multi-molecular complex such as a dimer, trimer or tetramer. In some embodiments, an antigen comprises a single chain polypeptide or multichain polypeptides and may be associated with or linked to each other, e.g., through a disulfide linkage. The term "polypeptide" applies to amino acid polymers, including naturally-occurring amino acid, as well as amino acid polymers in which at least one amino acid residue is an artificial chemical analogue of a corresponding naturally-occurring amino acid.

Antigens, in some embodiments, may be variants of a naturally-occurring (native) antigen. An "antigen variant" is an antigen that differs in its amino acid sequence relative to a native sequence or a reference sequence. Amino acid sequence variants may possess substitutions, deletions, insertions, or a combination of any two or three of the foregoing, at certain positions within the amino acid sequence, as compared to a native sequence or a reference sequence. In some embodiments, a variant possess at least 50% identity to a native sequence or a reference sequence. In some embodiments, variants share at least 60%, at least 70%, at least 80%, or at least 90% identity with a native sequence or a reference sequence.

Thus, mRNA encoding antigens containing substitutions, insertions, deletions, and/or covalent modifications with respect to reference antigens (e.g., native antigens) are included within the scope of this disclosure.

In some embodiments, sequence tags or amino acids, such as lysine(s), can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal residues or N-terminal residues) alternatively may be deleted depending on the use of the sequence, as for example, expression of the sequence as part of a larger sequence that is soluble, or linked to a solid support.

"Substitutional variants" when referring to antigens are those that have at least one amino acid residue in a native or starting sequence removed and a different amino acid inserted in its place at the same position. Substitutions may be single, where only one amino acid in the molecule has been substituted, or they may be multiple, where two or more (e.g., 3, 4 or 5) amino acids have been substituted in the same molecule.

A "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptides (e.g., antigens) and polynucleotides (e.g., mRNA) are defined as distinct amino acid sequence-based or nucleotide-based components of the molecule, respectively. Features of polypeptides encoded by polynucleotides include surface manifestations, local conformational shape, folds, loops, half-loops, domains, half-domains, sites, termini and any combination(s) thereof.

When referring to polypeptides, the term "domain" refers to a motif of a polypeptide having at least one identifiable structural or functional characteristics or properties (e.g., binding capacity, serving as a site for protein-protein interactions).

When referring to polypeptides, the term "site" as it pertains to amino acid based embodiments is used synonymously with "amino acid residue" and "amino acid side chain." When referring to polynucleotides, the term "site" as it pertains to nucleotide based embodiments is used synonymously with "nucleotide." A site represents a position within a polypeptide or polynucleotide that may be modified, manipulated, altered, derivatized or varied within the polypeptide-based or polynucleotide-based molecules.

The terms "termini" or "terminus" when referring to polypeptides or polynucleotides refers to an extremity of a polypeptide or polynucleotide, respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

Protein fragments, functional protein domains, and homologous proteins are also considered to be within the scope of polypeptides (e.g., antigens) of interest. For example, provided herein is any protein fragment (meaning a polypeptide sequence at least one amino acid residue shorter than a reference polypeptide sequence but otherwise identical) of a reference protein having a length of 10, 20, 30, 40, 50, 60, 70, 80, 90, 100 or longer than 100 amino acids. In another example, any protein that includes a stretch of 20, 30, 40, 50, or 100 (contiguous) amino acids that are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided herein or referenced herein. In another example, any protein that includes a stretch of 20, 30, 40, 50, or 100 amino acids that are greater than 80%, 90%, 95%, or 100% identical to any of the sequences described herein, wherein the protein has a stretch of 5, 10, 15, 20, 25, or 30 amino acids that are less than 80%, 75%, 70%, 65% to 60% identical to any of the sequences described herein can be utilized in accordance with the disclosure.

Viral Antigens

In some embodiments, an antigen is a viral antigen. A "viral antigen" is an antigen encoded by a viral genome. In some embodiments, an immunogenic composition of the present disclosure comprises a mRNA encoding a viral antigen. In some embodiments, an immunogenic composition comprises a cationic lipid nanoparticle (LNP) encapsulating mRNA having an open reading frame encoding at least one viral antigen, a pan HLA DR-binding epitope (PADRE), and a 5' terminal cap modified to increase mRNA translation efficiency. In some embodiments, the cationic lipid nanoparticle comprises a cationic lipid, a PEG-modified lipid, a sterol and a non-cationic lipid. Examples of viral antigens include, but are not limited to, Betacoronavirus, Chikungunya virus, Dengue virus, Ebola virus, Eastern Equine Encephalitis virus, Herpes Simplex virus, Human Cytomegalovirus, Human Papillomavirus. Human Metapneumovirus, Influenza virus, Japanese Encephalitis virus, Marburg virus, Measles, Parainfluenza virus, Respiratory Syncytial virus, Sindbis virus, Varicella Zoster virus. Venezuelan Equine Encephalitis virus, West Nile virus, Yellow Fever virus, and Zika virus antigens.

Betacoronavirus. In some embodiments, the BetaCoV is MERS-CoV. In some embodiments, the BetaCoV is SARS-CoV. In some embodiments, the BetaCoV is HCoV-OC43. In some embodiments, the BetaCoV is HCoV-229E. In some embodiments, the BetaCoV is HCoV-NL63. In some embodiments, the BetaCoV is HCoV-HKU1. In some embodiments, at least one antigen encoded by an mRNA of an immunogenic composition is a betacoronavirus structural protein. For example, at least one antigen may be spike protein (S), envelope protein (E), nucleocapsid protein (N), membrane protein (M) or an immunogenic fragment thereof. In some embodiments, at least one antigen is a spike protein (S). In some embodiments, at least one antigen is a S1 subunit or a S2 subunit of spike protein (S) or an immunogenic fragment thereof. In some embodiments, at least one antigen is at least one accessory protein (e.g., protein 3, protein 4a, protein 4b, protein 5), at least one replicase protein (e.g., protein 1a, protein 1b), or a combination of at least one accessory protein and at least one replicase protein.

Chikungunya virus. In some embodiments, at least one antigen encoded by an mRNA of an immunogenic composition is a CHIKV structural protein selected from an envelope protein (E) (e.g, E1, E2, E3), a 6K protein, or a capsid (C) protein.

Dengue virus. In some embodiments, at least one antigen encoded by an mRNA of an immunogenic composition is a DENV capsid protein, a DENV membrane protein, a DENV precursor-membrane protein, a DENV precursor membrane (prM) and envelope (E) polypeptide (DENV prME), or a DENV non-structural protein selected from NS1, NS2A, NS2B, NS3, NS4A, NS4B, and NS5. In some embodiments, at least one antigen is from a DENV serotype selected from DENV-1. DENV-2, DENV-3, DENV-4, and DENV-5.

Ebola virus. In some embodiments, at least one antigen encoded by an mRNA of an immunogenic composition is EBOV glycoprotein (GP), surface EBOV GP, wild type EBOV pro-GP, mature EBOV GP, secreted wild type EBOV pro-GP, secreted mature EBOV GP, EBOV nucleoprotein (NP), RNA polymerase L, and EBOV matrix protein selected from VP35, VP40, VP24, or VP30. In some embodiments, at least one antigen encoded by an mRNA of an immunogenic composition is EBOV glycoprotein (GP), surface EBOV GP, wild type EBOV GP, mature EBOV GP, secreted wild type EBOV GP, secreted mature EBOV GP, sGP, delta peptide (Δ-peptide), GP1, GP1, 2Δ, nucleoprotein NP, viral polymerase L, the polymerase cofactor VP35, the transcriptional activator VP30, VP24, or the matrix protein VP40.

Herpes Simplex virus. In some embodiments, at least one antigen encoded by an mRNA of an immunogenic composition is HSV (HSV-1 or HSV-2) glycoprotein B, HSV (HSV-1 or HSV-2) glycoprotein C, HSV (HSV-1 or HSV-2) glycoprotein D. HSV (HSV-1 or HSV-2) glycoprotein E, or HSV (HSV-1 or HSV-2) glycoprotein I.

Human Cytomegalovirus. In some embodiments, at least one antigen encoded by an mRNA of an immunogenic composition is a HCMV gH, gL, gB, gO, gN, gM, UL83, UL123, UL128, ULl30, or UL131A protein.

Human Papillomavirus. In some embodiments, at least one antigen encoded by an mRNA of an immunogenic composition is E1, E2, E4, E5, E6, E7, L1, and L2, e.g., obtained from HPV serotypes 6, 11, 16, 18, 31, 33, 35, 39, 45, 51, 52, 56, 58, 59, 68, 73 or 82.

Human Metapneumovirus, Parainfluenza virus and Respiratory Syncytial virus. In some embodiments, at least one antigen encoded by an mRNA of an immunogenic composition is major surface glycoprotein G or an immunogenic fragment thereof. In some embodiments, at least one antigen is Fusion (F) glycoprotein (e.g., Fusion glycoprotein F0, F1 or F2) or an immunogenic fragment thereof. In some embodiments, at least one antigen is major surface glycoprotein G or an immunogenic fragment thereof and F glycoprotein or an immunogenic fragment thereof. In some embodiments, at least one antigen is nucleoprotein (N) or an immunogenic fragment thereof, phosphoprotein (P) or an immunogenic fragment thereof, large polymerase protein (L) or an immunogenic fragment thereof, matrix protein (M) or an immunogenic fragment thereof, small hydrophobic protein (SH) or an immunogenic fragment thereof, nonstructural protein1 (NS1) or an immunogenic fragment thereof, or nonstructural protein 2 (NS2) and an immunogenic fragment thereof.

Influenza virus. In some embodiments, at least one antigen encoded by an mRNA of an immunogenic composition is an antigenic subdomains of HA, termed HA1, HA2, or a combination of HA1 and HA2 (or a combination of both, of any one of or a combination of any or all of H1, H2, H3, H4, H5, H6, H7, H8, H9, H10, H11, H12, H13, H14, H15, H16, H17, and/or H18), and at least one antigenic polypeptide selected from neuraminidase (NA), nucleoprotein (NP), matrix protein 1 (M1), matrix protein 2 (M2), non-structural protein 1 (NS1) and non-structural protein 2 (NS2).

Japanese Encephalitis virus. In some embodiments, at least one antigen encoded by an mRNA of an immunogenic composition is JEV E protein, JEV Es, JEV prM, JEV capsid, JEV NS1, or JEV prM and E polyprotein (prME).

Marburg virus. In some embodiments, at least one antigen encoded by an mRNA of an immunogenic composition is a MARV glycoprotein (GP).

Measles. In some embodiments, at least one antigen encoded by an mRNA of an immunogenic composition is a hemagglutinin (HA) protein or an immunogenic fragment thereof. The HA protein may be from MeV strain D3 or B8, for example. In some embodiments, at least one antigen is a Fusion (F) protein or an immunogenic fragment thereof. The F protein may be from MeV strain D3 or B8, for example. In some embodiments, at least one antigen comprises a HA protein and a F protein. The HA and F proteins may be from MeV strain D3 or B8, for example.

Varicella Zoster virus. In some embodiments, at least one antigen encoded by an mRNA of an immunogenic composition is a VZV glycoprotein selected from VZV gE, gi, gB, gH, gK, gL, gC, gN, and gM.

West Nile virus, Eastern Equine Encephalitis virus, Venezuelan Equine Encephalitis virus, and Sindbis virus. In some embodiments, at least one antigen encoded by an mRNA of an immunogenic composition is at least one Arbovirus antigen and/or at least one Alphavirus antigen.

Yellow Fever virus. In some embodiments, at least one antigen encoded by an mRNA of an immunogenic composition is a YFV polyprotein, a YFV capsid protein, a YFV premembrane/membrane protein, a YFV envelope protein, a YFV non-structural protein 1, a YFV non-structural protein 2A, a YFV non-structural protein 2B, a YFV non-structural protein 3, a YFV non-structural protein 4A, a YFV non-structural protein 4B, or a YFV non-structural protein 5.

Zika virus antigens. In some embodiments, at least one antigen encoded by an mRNA of an immunogenic composition is a ZIKV polyprotein, a ZIKV capsid protein, a ZIKV premembrane/membrane protein, a ZIKV envelope protein, a ZIKV non-structural protein 1, a ZIKV non-structural protein 2A, a ZIKV non-structural protein 2B, a ZIKV non-structural protein 3, a ZIKV non-structural protein 4A, a ZIKV non-structural protein 4B, or a ZIKV non-structural protein 5.

In some embodiments, the ZIKV antigen comprises the following amino acid sequence:

```
                              (WT ZIKV prME, (SEQ ID NO: 2)
AEVTRRGSAYYMYLDRNDAGEAISFPTTLGMNKCYIQIMDLGHMCDATMS

YECPMLDEGVEPDDVDCWCNTTSTWVVYGTCHHKKGEARRSRRAVTLPSH

STRKLQTRSQTWLESREYTKHLIRVENWIFRNPGFALAAAAIAWLLGSST

SQKVIYLVMILLIAPAYSIRCIGVSNRDFVEGMSGGTWVDVVLEHGGCVT

VMAQDKPTVDIELVTTTVSNMAEVRSYCYEASISDMASDSRCPTQGEAYL
```

-continued
DKQSDTQYVCKRTLVDRGWGNGCGLFGKGSLVTCAKFACSKKMTGKSIQP

ENLEYRIMLSVHGSQHSGMIVNDTGHETDENRAKVEITPNSPRAEATLGG

FGSLGLDCEPRTGLDFSDLYYLTMNNKHWLVHKEWFHDIPLPWHAGADTG

TPHWNNKEALVEFKDAHAKRQTVVVLGSQEGAVHTALAGALEAEMDGAKG

RLSSGHLKCRLKMDKLRLKGVSYSLCTAAFTFTKIPAETLHGTVTVEVQY

ADTDGPCKVPAQMAVDMQTLTPVGRLITANPVITESTENSKMMLELDPPF

GDSYIVIGVGEKKITHHWHRSGSTIGKAFEATVRGAKRMAVLGDTAWDFG

SVGGALNSLGKGIHQIFGAAFKSLFGGMSWFSQILIGTLLMWLGLNTKNG

SISLMCLALGGVLIFLSTAVSA.

In some embodiments, SEQ ID NO: 2 is fused to a

PADRE sequence (e.g., SEQ ID NO: 1).

In some embodiments, the ZIKV antigen comprises the following amino acid sequence:

```
          (WT ZIKV prME, JEVprM signal; SEQ ID NO: 3)
MWLVSLAIVTACAGA AEVTRRGSAYYMYLDRNDAGEAISFPTTLGMNKCY
```
IQIMDLGHMCDATMSYECPMLDEGVEPDDVDCWCNTTSTWVVYGTCHHKK

GEARRSRRAVTLPSHSTRKLQTRSQTWLESREYTKHLIRVENWIFRNPGF

ALAAAAIAWLLGSSTSQKVIYLVMILLIAPAYSIRCIGVSNRDFVEGMSG

GTWVDVVLEHGGCVTVMAQDKPTVDIELVTTTVSNMAEVRSYCYEASISD

MASDSRCPTQGEAYLDKQSDTQYVCKRTLVDRGWGNGCGLFGKGSLVTCA

KFACSKKMTGKSIQPENLEYRIMLSVHGSQHSGMIVNDTGHETDENRAKV

EITPNSPRAEATLGGFGSLGLDCEPRTGLDFSDLYYLTMNNKHWLVHKEW

FHDIPLPWHAGADTGTPHWNNKEALVEFKDAHAKRQTVVVLGSQEGAVHT

ALAGALEAEMDGAKGRLSSGHLKCRLKMDKLRLKGVSYSLCTAAFTFTKI

PAETLHGTVTVEVQYAGTDGPCKVPAQMAVDMQTLTPVGRLITANPVITE

STENSKMMLELDPPFGDSYIVIGVGEKKITHHWHRSGSTIGKAFEATVRG

AKRMAVLGDTAWDFGSVGGALNSLGKGIHQIFGAAFKSLFGGMSWFSQIL

IGTLLMWLGLNTKNGSISLMCLALGGVLIFLSTAVSA.

In some embodiments. SEQ ID NO: 3 is fused to a PADRE sequence (e.g., SEQ ID NO: 1).

In some embodiments, the ZIKV antigen comprises the following amino acid sequence:

```
                     (Modified ZIKV prME; SEQ ID NO: 4)
AEVTRRGSAYYMYLDRNDAGEAISFPTTLGMNKCYIQIMDLGHMCDATMS
```
YECPMLDEGVEPDDVDCWCNTTSTWVVYGTCHHKKGEARRSRRAVTLPSH

STRKLQTRSQTWLESREYTKHLIRVENWIFRNPGFALAAAAIAWLLGSST

SQKVIYLVMILLIAPAYSIRCIGVSNRDFVEGMSGGTWVDVVLEHGGCVT

VMAQDKPTVDIELVTTTVSNMAEVRSYCYEASISDMASDSRCPREGEAYL

DKQSDTQYVCKRTLVDRGRGNGCGRFGKGSLVTCAKFACSKKMTGKSIQP

ENLEURIMLSVHGSQHSGMIVNDTGHETDENRAKVEITPNSPRAEATLGG

FGSLGLDCEPRTGLDFSDLYYLTMNNKHWLVHKEWFHDIPLPWHAGADTG

TPHWNNKEALVEFKDAHQKRQTVVVLGSQEGAVHTALAGALEAEMDGAKG

-continued
RLSSGHLKCRLKMDKLRLKGVSYSLCTAAFTFTKIPAETLHGTVTVEVQY

AGTDGPCKVPAQMAVDMQTLTPVGRLITANPVITESTENSKMMLELDPPF

GDSYIVIGVGEKKITHHWHRSGSTIGKAFEATVRGAKRMAVLGDTAWDFG

SVGGALNSLGKGIHQIFGAAFKSLFGGMSWFSQILIGTLLMWLGLNTKNG

SISLMCLALGGVLIFLSTAVSA.

In some embodiments, SEQ ID NO: 4 is fused to a PADRE sequence (e.g., SEQ ID NO: 1).

In some embodiments, the ZIKV antigen comprises the following amino acid sequence:

```
         (Modified ZIKV prME, JEVprM signal; SEQ ID NO: 5)
MWLVSLAIVTACAGA AEVTRRGSAYYMYLDRNDAGEAISFPTTLGMNKCY
```
IQIMDLGHMCDATMSYECPMLDEGVEPDDVDCWCNTTSTWVVYGTCHHKK

GEARRSRRAVTLPSHSTRKLQTRSQTWLESREYTKHLIRVENWIFRNPGF

ALAAAAIAWLLGSSTSQKVIYLVMILLIAPAYSIRCIGVSNRDFVEMGSG

GTWVDVVLEHGGCVTVMAQDKPTVDIELVTTTVSNMAEVRSYCYEASISD

MASDSRVPREGEAYLDKQSDTQYVCKRTLVDRGRGNGCGRFGKGSLVTCA

KFACSKKMTGKSIQPENLEYRIMLSVHGSQHSGMIVNDTGEHETDENRAK

VEITPNSPRAEATLGGFGSLGLDCEPRTGLDFSDLYYLTMNNKHWLVHKE

WFHDIPLPWHAGADTGTPHWNNKEALVEFKDAHAKRQTVVVLGSQEGAVH

TALAGALEAEMDGAKGRLSSGHLKCRLKMDKLRLKGVSYSLCTAAFTFTK

IPAETLHGTVTVEVQYAGTDGPCKVPAQMAVDMQTLTPVGRLITANPVIT

ESTENSKMMLELDPPFGDSYIVIGVGEKKITHHWHRSGSTIGKAFEATVR

GAKRMAVLGDTAWDFGSVGGALNSLGKGIHQIFGAAFKSLFGGMSWFSQI

LIGTLLMWLGLNTKGSISLMCLALGGVLIFLSTAVSA.

In some embodiments, SEQ ID NO: 5 is fused to a PADRE sequence (e.g., SEQ ID NO: 1).

In some embodiments, the ZIKV antigen comprises the following amino acid sequence:

```
                (Modified ZIKV prME, IgE; SEQ ID NO: 6)
MDWTWILFLVAAATRVHS AEVTRRGSAYYMYLDRNDAGEAISFPTTLGMN
```
KCYIQIMDLGHMCDATMSYECPMLDEGVEPDDVDCWCNTTSTWVVYGTCH

HKKGEARRSRRAVTLPSHSTRKLQTRSQTWLESREYTKHLIRVENWIFRN

PGFALAAAAIAWLLGSSTSQKVIYLVMILLIAPAYSIRCIGVSNRDFVEG

MSGGTWVDVVLEHGGCVTVMAQDKPTVDIELVTTTVSNMAEVRSYCYEAS

ISDMASDSRCPREGEAYLDKQSDTQYVCKRTLVDRGRGNGCGRFGKGSLV

TCAKFACSKKMTGKSIQPENLEYRIMLSVHGSQHSGMIVNDTGHETDENR

AKVEITPNSPRAEATLGGFGSLGLDCEPRTGLDFSDLYYLTMNNKWHLVH

KEWFHDIPLPWHAGADTGTPHWNNKEALVEFKDAHAKRQTVVVLQSQEGA

VHTALAGALEAEMDGAKGRLSSGHLKCRLKMDKLRLKGVSYSLCTAAFTF

TKIPAETLHGTVTVEVQYAGTDGPCKVPAQMAVDMQTLTPVGRLITANPV

ITESTENSKMMLELDPPFGDSYIVIGVGEKKITHHWHRSGSTIGKAFEAT

-continued

VRGAKRMAVLGDTAWDFGSVGGALNSLGKGIHQIFGAAFKSLFGGMSWFS

QILIGTLLMWLGLNTKNGSISLMCLALGGVLIFLSTAVSA.

In some embodiments, SEQ ID NO: 6 is fused to a PADRE sequence (e.g., SEQ ID NO: 1).

Bacterial Antigens.

In some embodiments, an antigen is a bacterial antigen. A "bacterial antigen" is an antigen encoded by a bacterial genome. In some embodiments, an immunogenic composition of the present disclosure comprises a mRNA encoding a bacterial antigen. In some embodiments, an immunogenic composition comprises a cationic lipid nanoparticle (LNP) encapsulating mRNA having an open reading frame encoding at least one bacterial antigen, a pan HLA DR-binding epitope (PADRE), and a 5' terminal cap modified to increase mRNA translation efficiency. In some embodiments, the cationic lipid nanoparticle comprises a cationic lipid, a PEG-modified lipid, a sterol and a non-cationic lipid. Examples of bacterial antigens include, but are not limited to, *Chlamydia trachomatis* antigen, a Lyme *Borrelia* and a *Streptococcal* antigen.

In some embodiments, at least one antigen encoded by an mRNA of an immunogenic composition is a major outer membrane protein (MOMP or OmpA), e.g., from *Chlamydia trachomatis* serovar (serotype) H, F, E, D, I, G, J or K.

In some embodiments, at least one antigen encoded by an mRNA of an immunogenic composition is a *Borrelia* OspA protein.

Parasitic Antigens.

In some embodiments, an antigen is a parasitic antigen. A "parasitic antigen" is an antigen encoded by a parasitic genome. In some embodiments, an immunogenic composition of the present disclosure comprises a mRNA encoding a parasitic antigen. In some embodiments, an immunogenic composition comprises a cationic lipid nanoparticle (LNP) encapsulating mRNA having an open reading frame encoding at least one parasitic antigen, a pan HLA DR-binding epitope (PADRE), and a 5' terminal cap modified to increase mRNA translation efficiency. In some embodiments, the cationic lipid nanoparticle comprises a cationic lipid, a PEG-modified lipid, a sterol and a non-cationic lipid. Examples of parasitic antigens include, but are not limited to, *Plasmodium falciparum, Plasmodium vivax, Plasmodium ovale*, and *Plasmodium malariae*, and *Plasmodium knowlesi* antigens.

In some embodiments, at least one antigen encoded by an mRNA of an immunogenic composition is a circumsporozoite (CS) protein or an immunogenic fragment thereof (e.g., capable of raising an immune response against Plasmodium). In some embodiments, at least one antigen is RTS hybrid protein. In some embodiments, at least one antigen is merozoite surface protein-1 (MSP1), apical membrane antigen 1 (AMA1), or thrombospondin related adhesive protein (TRAP) or an immunogenic fragment thereof.

Chemically Unmodified Nucleotides

In some embodiments, at least one RNA (e.g., mRNA) of the vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications the RNA vaccines of the present disclosure comprise, in some embodiments, at least one nucleic acid (e.g., RNA) having an open reading frame encoding at least one antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethylpseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises 1-methyl-pseudouridine (m1ψ) substitutions at one or more or all uridine positions of the nucleic acid.

In some embodiments, a RNA nucleic acid of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1%to 20%, from 1% to 25%, from 1% to 50%, from 1% to 60%, from 1% to 70%, from 1% to 80%, from 1% to 90%, from 1% to 95%, from 10% to 20%0 from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 200% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100% from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Untranslated Regions (UTRs)

The nucleic acids of the present disclosure may comprise one or more regions or parts which act or function as an untranslated region. Where nucleic acids are designed to encode at least one antigen of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 12), where R is a purine (adenine or guanine) three bases upstream of the start codon (AUG), which is followed by another 'G'.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include Xenopus or human derived a-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US2014/0206753, WO2013/185069), the sequence GGGAUCCUACC (SEQ ID NO: 13) (WO2014/144196) may also be used. In another embodiment, 5' UTR of a TOP gene is a 5' UTR of a TOP gene lacking the 5' TOP motif (the oligopyrimidine tract) (e.g., WO2015/101414, WO2015/101415, WO2015/062738, WO2015/024667, WO2015/024667); 5' UTR element derived from ribosomal protein Large 32 (L32) gene (WO2015/101414, WO2015/101415, WO2015/062738), 5' UTR element derived from the 5'UTR of an hydroxysteroid (17-β) dehydrogenase 4 gene (HSD17B4) (WO2015/024667), or a 5' UTR element derived from the 5' UTR of ATP5A1 (WO2015/024667) can be used. In some embodiments, an internal ribosome entry site (IRES) is used instead of a 5' UTR.

A 3' UTR is region of an mRNA that is directly downstream (3') from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 14) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

3' UTRs may be heterologous or synthetic. With respect to 3' UTRs, globin UTRs, including Xenopus β-globin UTRs and human β-globin UTRs are known in the art (U.S. Pat. Nos. 8,278,063, 9,012,219, US2011/0086907). A modified β-globin construct with enhanced stability in some cell types by cloning two sequential human β-globin 3'UTRs head to tail has been developed and is well known in the art (US2012/0195936, WO2014/071963). In addition a2-globin, a1-globin, UTRs and mutants thereof are also known in the art (WO2015/101415, WO2015/024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US2014/0206753, WO2014/152774), rabbit β globin and hepatitis B virus (HBV), α-globin 3' UTR and Viral VEEV 3' UTR sequences are also known in the art. In some embodiments, the sequence UUUGAAUU (WO2014/144196) is used. In some embodiments, 3' UTRs of human and mouse ribosomal protein are used. Other examples include rps9 3'UTR (WO2015/101414), FIG. 4 (WO2015/101415), and human albumin 7 (WO2015/101415).

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 2010/0293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 2010/0129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Patent Publication No. 2009/0226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO2014/152027, which is incorporated by reference herein in its entirety.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of a RNA polynucleotide, for example, but not limited to infectious disease (e.g., ZIKV) RNA, e.g. mRNA. In some embodiments, cells, e.g., bacterial cells, e.g., E. coli, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')N1mpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, Mass.), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR Quantification In some embodiments, the nucleic acids of the present invention may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (Thermo-Fisher, Waltham, Mass.). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/

027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound of Formula (I):

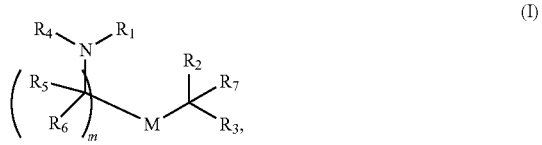

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —CXH_2, —CN, —N$(R)_2$, —C(O)N$(R)_2$, —N(R)C(O)R, —N(R)S(O)_2R, —N(R)C(O)N$(R)_2$, —N(R)C(S)N$(R)_2$, —N(R)R_8, —O(CH_2)_nOR, —N(R)C(=NR_9)N$(R)_2$, —N(R)C(=CHR_9)N$(R)_2$, —OC(O)N$(R)_2$, —N(R)C(O)OR, —N(OR)C(O)R, —N(OR)S(O)_2 R, —N(OR)C(O)OR, —N(OR)C(O)N$(R)_2$, —N(OR)C(S)N$(R)_2$, —N(OR)C(=NR_9)N$(R)_2$, —N(OR)C(=CHR_9)N$(R)_2$, —C(=NR_9)N$(R)_2$, —C(=NR_9)R, —C(O)N(R)OR, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)_2—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)_2R, —S(O)_2N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ is alkyl, $C_{2-18}$ alkenyl, —R*YR", —YR", and H;

each R" is independently selected from the group consisting of $C_{3-14}$ alkyl and $C_{1-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —CXH_2, —CN, —C(O)N$(R)_2$, —N(R)C(O)R, —N(R)S(O)_2R, —N(R)C(O)N$(R)_2$, —N(R)C(S)N$(R)_2$, —CRN$(R)_2$C(O)OR, —N(R)R_8, —O(CH_2)_nOR, —N(R)C(=NR_9)N$(R)_2$, —N(R)C(=CHR_9)N$(R)_2$, —OC(O)N$(R)_2$, —N(R)C(O)OR, —N(OR)C(O)R, —N(OR)S(O)_2R, —N(OR)C(O)OR, —N(OR)C(O)N$(R)_2$, —N(OR)C(S)N$(R)_2$, —N(OR)C(=NR_9)N$(R)_2$, —N(OR)C(=CHR_9)N$(R)_2$, —C(=NR_9)N$(R)_2$, —C(=NR_9)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ is alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR', and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ is alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl, each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

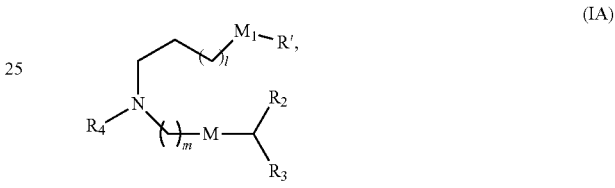

(IA)

or a salt or isomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —C(O)N(R')—, —P(O)(OR')O—, —S—S—, an aryl group, and a heteroaryl group, and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

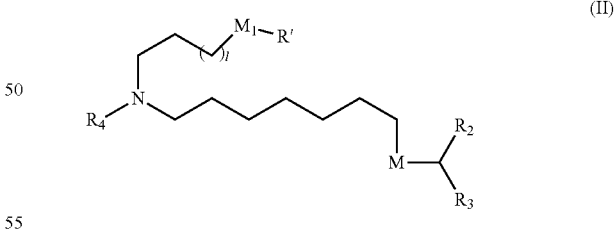

(II)

or a salt or isomer thereof, wherein l is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —$NHC(S)N(R)_2$, —$NHC(O)N(R)_2$, —$N(R)C(O)R$, —$N(R)S(O)_2R$, —$N(R)R_8$, —$NHC(=NR_9)N(R)_2$, —$NHC(=CHR_9)N(R)_2$, —$OC(O)N(R)_2$, —$N(R)C(O)OR$, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

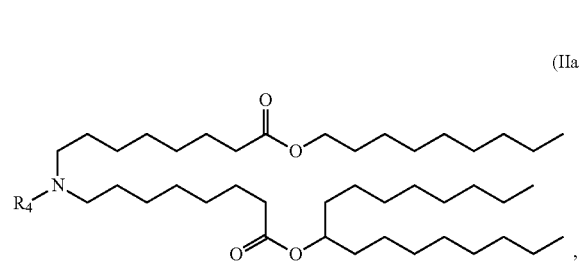
(IIa)

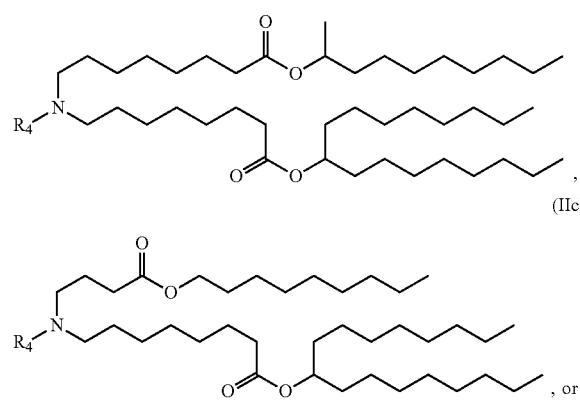
(IIb)

, (IIc)

, or

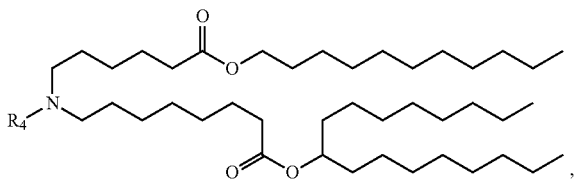
(IIe)

or a salt or isomer thereof, wherein $R_4$ is as described herein.

In some embodiments, a subset of compounds of Formula (I) includes those of Formula (IId):

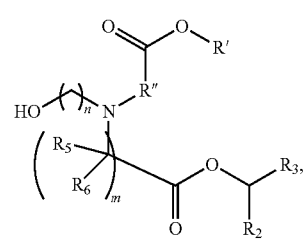
(IId)

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

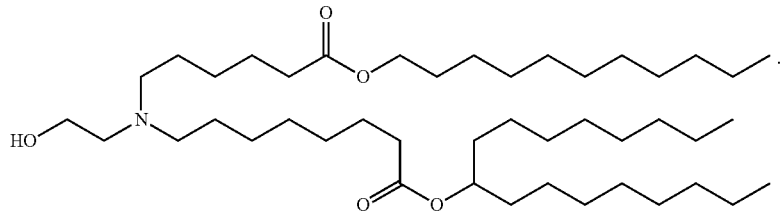
(Compound 1)

In some embodiments, an ionizable cationic lipid of the disclosure comprises a compound having structure:

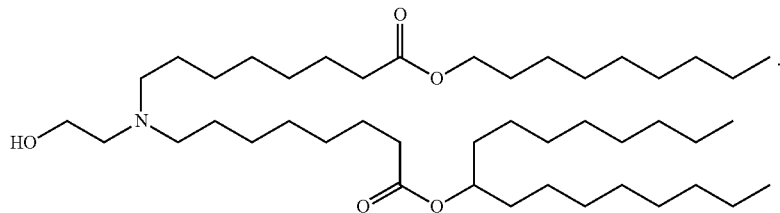
(Compound 2)

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-3-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Signal Sequences/Peptides

In some embodiments, an antigen and/or a PADRE encoded by a mRNA of the present disclosure comprises a signal peptide. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. Signal peptides generally include three regions: an N-terminal region of differing length, which usually comprises positively charged amino acids; a hydrophobic region; and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane. The signal peptide, however, is not responsible for the final destination of the mature protein. Secretory proteins devoid of additional address tags in their sequence are by default secreted to the external environment. During recent years, a more advanced view of signal peptides has evolved, showing that the functions and immunodominance of certain signal peptides are much more versatile than previously anticipated.

Immunogenic compositions of the present disclosure may comprise, for example, mRNA encoding an artificial signal peptide, wherein the signal peptide coding sequence is operably linked to and is in frame with the coding sequence of the antigen and/or PADRE. Thus, mRNA of the present disclosure, in some embodiments, produce an antigen and/or a PADRE fused to a signal peptide. In some embodiments, a signal peptide is fused to the N-terminus of the antigen and/or a PADRE. In some embodiments, a signal peptide is fused to the C-terminus of the antigen and/or a PADRE.

In some embodiments, the signal peptide fused to the antigen and/or a PADRE is an artificial signal peptide. In some embodiments, a signal peptide fused to the antigen and/or a PADRE encoded by the mRNA is a HuIgGk signal peptide (METPAQLLFLLLLWLPDTTG; SEQ ID NO: 7). In some embodiments, a signal peptide fused to the antigen and/or a PADRE encoded by the mRNA is a IgE heavy chain epsilon-1 signal peptide (MDWTWILFLVAAATRVHS; SEQ ID NO: 8). In some embodiments, a signal peptide fused to the antigen and/or a PADRE encoded by the mRNA is a JEV polyprotein signal peptide (MLGSNSGQRV-VFTILLLLVAPAYS; SEQ ID NO: 9). In some embodiments, a signal peptide fused to the antigen and/or a PADRE encoded by the mRNA is a VSVg protein signal peptide (MKCLLYLAFLFIGVNCA SEQ ID NO: 10. In some embodiments, a signal peptide fused to the antigen and/or a PADRE encoded by the mRNA is a Japanese encephalitis prM signal peptide (MWLVSLAIVTACAGA; SEQ ID NO: 11).

The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

A signal peptide is typically cleaved from the nascent polypeptide at the cleavage junction during ER processing. The mature antigen and/or a PADRE encoded by the mRNA of the present disclosure typically does not comprise a signal peptide.

Fusion Proteins

In some embodiments, an the RNA vaccine of the present disclosure includes an RNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the antigen. Antigenic fusion proteins, in some embodiments, retain the functional property from each original protein.

Scaffold Moieties

The RNA (e.g., mRNA) vaccines as provided herein, in some embodiments, encode fusion proteins which comprise the antigens linked to scaffold moieties. In some embodiments, such scaffold moieties impart desired properties to an antigen encoded by a nucleic acid of the disclosure. For example scaffold proteins may improve the immunogenicity of an antigen, e.g., by altering the structure of the antigen, altering the uptake and processing of the antigen, and/or causing the antigen to bind to a binding partner.

In some embodiments, the scaffold moiety is protein that can self-assemble into protein nanoparticles that are highly symmetric, stable, and structurally organized, with diameters of 10-150 nm, a highly suitable size range for optimal interactions with various cells of the immune system. In some embodiments, viral proteins or virus-like particles can be used to form stable nanoparticle structures. Examples of such viral proteins are known in the art. For example, in some embodiments, the scaffold moiety is a hepatitis B surface antigen (HBsAg). HBsAg forms spherical particles with an average diameter of ~22 nm and which lacked nucleic acid and hence are non-infectious (Lopez-Sagaseta. J. et al. *Computational and Structural Biotechnology Journal* 14 (2016) 58-68). In some embodiments, the scaffold moiety is a hepatitis B core antigen (HBcAg) self-assembles into particles of 24-31 nm diameter, which resembled the viral cores obtained from HBV-infected human liver. HBcAg produced in self-assembles into two classes of differently sized nanoparticles of 300 Å and 360 Å diameter, corresponding to 180 or 240 protomers. In some embodiments an the antigen is fused to HBsAG or HBcAG to facilitate self-assembly of nanoparticles displaying the antigen.

In another embodiment, bacterial protein platforms may be used. Non-limiting examples of these self-assembling proteins include ferritin, lumazine and encapsulin.

Ferritin is a protein whose main function is intracellular iron storage. Ferritin is made of 24 subunits, each composed of a four-alpha-helix bundle, that self-assemble in a quaternary structure with octahedral symmetry (Cho K. J. et al. *J Mol Biol*. 2009;390:83-98). Several high-resolution structures of ferritin have been determined, confirming that *Helicobacter pylori* ferritin is made of 24 identical protomers, whereas in animals, there are ferritin light and heavy chains that can assemble alone or combine with different ratios into particles of 24 subunits (Granier T. et al. *J Biol Inorg Chem*. 2003;8:105-111; Lawson D. M. et al. *Nature*. 1991;349:541-544). Ferritin self-assembles into nanoparticles with robust thermal and chemical stability. Thus, the ferritin nanoparticle is well-suited to carry and expose antigens.

Lumazine synthase (LS) is also well-suited as a nanoparticle platform for antigen display. LS, which is responsible for the penultimate catalytic step in the biosynthesis of riboflavin, is an enzyme present in a broad variety of organisms, including archaea, bacteria, fungi, plants, and eubacteria (Weber S. E. *Flavins and Flavoproteins*. Methods and Protocols, Series: Methods in Molecular Biology. 2014). The LS monomer is 150 amino acids long, and consists of beta-sheets along with tandem alpha-helices flanking its sides. A number of different quaternary structures have been reported for LS, illustrating its morphological versatility: from homopentamers up to symmetrical assemblies of 12 pentamers forming capsids of 150 Å diameter. Even LS cages of more than 100 subunits have been described (Zhang X. et al. *J Mol Biol*. 2006;362:753-770).

Encapsulin, a novel protein cage nanoparticle isolated from thermophile *Thermotoga maritima*, may also be used as a platform to present antigens on the surface of self-assembling nanoparticles. Encapsulin is assembled from 60 copies of identical 31 kDa monomers having a thin and icosahedral T=1 symmetric cage structure with interior and exterior diameters of 20 and 24 nm, respectively (Sutter M. et al. *Nat Struct Mol Biol*. 2008, 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses (Rahmanpour R. et al. *FEBS J*. 2013, 280: 2097-2104).

Linkers and Cleavable Peptides

In some embodiments, the mRNAs of the disclosure encode more than one polypeptide, referred to herein as fusion proteins. In some embodiments, the mRNA further encodes a linker located between at least one or each domain of the fusion protein. The linker can be, for example, a cleavable linker or protease-sensitive linker. In some embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) *PLoS ONE* 6:e18556). In some embodiments, the linker is an F2A linker. In some embodiments, the linker is a GGGS linker. In some embodiments, the fusion protein contains three domains with intervening linkers, having the structure: domain-linker-domain-linker-domain.

Cleavable linkers known in the art may be used in connection with the disclosure. Exemplary such linkers include: F2A linkers, T2A linkers, P2A linkers, E2A linkers (See, e.g., WO2017/127750). The skilled artisan will appreciate that other art-recognized linkers may be suitable for use in the constructs of the disclosure (e.g., encoded by the nucleic acids of the disclosure). The skilled artisan will likewise appreciate that other polycistronic constructs (mRNA encoding more than one antigen/polypeptide separately within the same molecule) may be suitable for use as provided herein.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures;

minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding an antigen). In some embodiments, a codon optimized sequence shares less than 90% sequence identity to a naturally-occurring or wild-type sequence (e.g., a naturally-occurring or wild-type mRNA sequence encoding an antigen). In some embodiments, a codon optimized sequence shares less than 85% sequence identity to a naturally-occurring or wild-type sequence (e.g., a naturally-occurring or wild-type mRNA sequence encoding an antigen). In some embodiments, a codon optimized sequence shares less than 80% sequence identity to a naturally-occurring or wild-type sequence (e.g., a naturally-occurring or wild-type mRNA sequence encoding an antigen). In some embodiments, a codon optimized sequence shares less than 75% sequence identity to a naturally-occurring or wild-type sequence (e.g., a naturally-occurring or wild-type mRNA sequence encoding an antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an antigen). In some embodiments, a codon optimized sequence shares between 65% and 75% or about 80% sequence identity to a naturally-occurring or wild-type sequence (e.g., a naturally-occurring or wild-type mRNA sequence encoding an antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than an antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than RNA containing a large amount of adenine (A) and thymine (T) or uracil (U) nucleotides. As an example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Pharmaceutical Formulations

Provided herein are compositions (e.g., pharmaceutical compositions), methods, kits and reagents for prevention or treatment of an infectious disease (e.g., ZIKV) in humans and other mammals, for example. The RNA (e.g., mRNA) vaccines can be used as therapeutic or prophylactic agents. They may be used in medicine to prevent and/or treat infectious disease.

In some embodiments, a vaccine containing RNA polynucleotides as described herein can be administered to a subject (e.g., a mammalian subject, such as a human subject), and the RNA polynucleotides are translated in vivo to produce an antigenic polypeptide (antigen).

An "effective amount" of a vaccine is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a vaccine provides an induced or boosted immune response as a function of antigen production in the cells of the subject. In some embodiments, an effective amount of the RNA vaccine containing RNA polynucleotides having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, RNA vaccines (including polynucleotides and their encoded polypeptides) in accordance with the present disclosure may be used for treatment or prevention of infectious disease (e.g., ZIKV), the RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

The RNA (e.g., mRNA) vaccines may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 4) years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, the RNA vaccines may be administered intramuscularly, intranasally or intradermally, similarly to the administration of inactivated vaccines known in the art.

The RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including the RNA vaccines and RNA vaccine compositions and/or complexes optionally in combination with one or more pharmaceutically acceptable excipients.

The RNA (e.g., mRNA) vaccines may be formulated or administered alone or in conjunction with one or more other components. For instance, the RNA vaccines (vaccine compositions) may comprise other components including, but not limited to, adjuvants.

In some embodiments, the RNA vaccines do not include an adjuvant (they are adjuvant free).

The RNA (e.g., mRNA) vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, the RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigens.

Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the RNA vaccines are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the RNA vaccines (e.g., for transplantation into a subject), hyaluronidase, nanoparticle mimics and combinations thereof.

Therapeutic and Prophylactic Compositions

Provided herein are compositions (e.g., pharmaceutical compositions), kits and reagents for prevention, treatment or diagnosis of an infection disease in humans and other mammals, for example. The immunogenic compositions of the present disclosure can be used as therapeutic agents or prophylactic agents. They may be used in medicine to prevent and/or treat infectious disease. In some embodiments, the immunogenic compositions are used in the priming of immune effector cells, for example, to activate peripheral blood mononuclear cells (PBMCs) ex vivo, which are then infused (re-infused) into a subject. In some embodiments, the immunogenic compositions are administered prophylactically or therapeutically as part of an active immunization scheme to healthy individuals or early in infection during the incubation phase or during active infection after onset of symptoms.

Typically, an immunogenic composition comprising mRNA encoding an antigen and/or PADRE is administered to a subject (e.g., a mammalian subject, such as a human subject), and the mRNA is translated in vivo (e.g., in a cell, tissue or organism) to produce the antigen and/or PADRE, although such translation may occur ex vivo, in culture or in vitro. In some embodiments, the cell, tissue or organism is contacted with an effective amount of an immunogenic composition containing mRNA that has at least one a translatable region encoding an antigen and/or PADRE.

An "effective amount" is a dose of an immunogenic composition (e.g., mRNA vaccine) effective to produce an antigen-specific immune response. An effective amount is based, at least in part, on the target tissue, target cell type, means of administration, physical characteristics of the polynucleotide (e.g., size, and extent of modified nucleosides) and other components of the composition, and other determinants. In general, an effective amount of an immunogenic composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the mRNA), increased protein translation from the polynucleotide, decreased nucleic acid degradation (as demonstrated, for example, by increased duration of protein translation from a modified polynucleotide), or altered antigen-specific immune response of the host cell. In some embodiments, the amount of an immunogenic composition provided to a cell, a tissue or a subject may be an amount effective for immune prophylaxis. In some embodiments, immunogenic compositions in accordance with the present disclosure may be used for treatment of infectious diseases, such as Zika virus.

In some embodiments, an effective amount of an immunogenic composition is a dose that is reduced compared to the standard of care dose of a recombinant protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified protein vaccine, or a live attenuated or inactivated viral vaccine, that a physician/clinician or other medical professional would administer to a subject to treat or prevent an infectious disease, while following the standard of care guideline for treating or preventing the infectious disease.

A "prophylactically effective amount" or a "prophylactically effective dose" is an effective amount that prevents infection with a virus, bacteria or parasite at a clinically acceptable level.

In some embodiments, an effective dose is a dose listed in a package insert for the vaccine. A traditional vaccine, as used herein, refers to a vaccine other than the immunogenic composition (e.g., mRNA vaccine) of the present disclosure. For instance, a traditional vaccine includes, but is not limited to, live/attenuated microorganism vaccines, killed/inactivated microorganism vaccines, subunit vaccines, protein antigen vaccines, DNA vaccines, and VLP vaccines. In some embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the effective amount of an immunogenic composition is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant protein vaccine.

In some embodiments, the anti-antigen antibody titer produced in the subject is equivalent to an anti-antigen antibody titer produced in a control subject administered the standard of care dose of a recombinant or purified protein vaccine, or a live attenuated or inactivated viral vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 570-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820--, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant protein vaccine. In some embodiments, an anti-antigen antibody titer produced in the subject is equivalent to an anti-antigen antibody titer produced in a control subject administered the standard of care dose of a recombinant or purified protein vaccine, or a live attenuated or inactivated viral vaccine.

In some embodiments, the effective amount is 5 µg-100 µg of the mRNA encoding the antigen and/or the PADRE. For example, the effective amount may be 5 µg-10 µg, 5 µg-20 µg, 5 µg-30 µg, 5 µg-40 µg, 5 µg-50 µg, 5 µg-60 µg, 5 µg-70 µg, 5 µg-80 µg, 5 µg-90 µg, 5 µg-100 µg, 10 µg-20 µg, 10 µg-30 µg, 10 µg-40 µg, 10 µg-50 µg, 10 µg-60 µg, 10 µg-70 µg, 10 µg-80 µg, 10 µg-90 µg, 10 µg-100 µg, 25 µg-30 µg, 25 µg-40 µg, 25 µg-50 µg, 25 µg-60 µg, 25 µg-70 µg, 25 µg-80 µg, 25 µg-90 µg, 25 µg-100 µg, 50 µg-60 µg, 50 µg-70 µg, 50 µg-80 µg, 50 µg-90 µg, or 50 µg-100 µg of the mRNA In some embodiments, the effective amount is 5 µg, 10 µg, 12.5 µg, 20 µg, 25 µg, 30 µg, 40 µg, 50 µg, 60 µg, 70 µg, 80 µg, 90 µg, 100 µg of the mRNA.

In some embodiments, a composition for or method of vaccinating a subject comprises administering to the subject a nucleic acid vaccine comprising at least one mRNA having an open reading frame encoding an infectious disease antigen (e.g., a viral, bacterial, and/or parasitic antigen) and/or a PADRE wherein a dosage of between 10 µg/kg and 400 µg/kg of the nucleic acid vaccine is administered to the subject. In some embodiments the dosage of the mRNA encoding the infectious disease antigen is 1-5 µg, 5-10 µg, 10-15 µg, 15-20 µg, 10-25 µg, 20-25 µg, 20-50 µg, 30-50 µg, 40-50 µg, 40-60 µg, 60-80 µg, 60-100 µg, 50-100 µg, 80-120 µg, 40-120 µg, 40-150 µg, 50-150 µg, 50-200 µg, 80-200 µg, 100-200 µg, 120-250 µg, 150-250 µg, 180-280 µg, 200-300 µg, 50-300 µg, 80-300 µg, 100-300 µg, 40-300 µg, 50-350 µg, 100-350 µg, 200-350 µg, 300-350 µg, 320-400 µg, 40-380 µg, 40-100 µg, 100-400 µg, 200-400 µg, or 300-400 µg per dose. In some embodiments the dosage of the mRNA encoding the PADRE is 1-5 µg, 5-10 µg, 10-15 µg, 15-20 µg, 10-25 µg, 20-25 µg, 20-50 µg, 30-50 µg, 40-50 µg, 40-60 µg, 60-80 µg, 60-100 µg, 50-100 µg, 80-120 µg, 40-120 µg, 40-150 µg, 50-150 µg, 50-200 µg, 80-200 µg, 100-200 µg, 120-250 µg, 150-250 µg, 180-280 µg, 200-300 µg, 50-300 µg, 80-300 µg, 100-30 µg, 40-300 µg, 50-350 µg, 100-350 µg, 200-350 µg, 300-350 µg, 320-400 µg, 40-380 µg, 40-100 µg, 100-400 µg, 200-400 µg, or 300-400 µg per dose. In some embodiments the dosage of the mRNA encoding the infectious disease antigen and the PADRE is 1-5 µg, 5-10 µg, 10-15 µg, 15-20 µg, 10-25 µg, 20-25 µg, 20-50 µg, 30-50 µg, 40-50 µg, 40-60 µg, 60-80 µg, 60-100 µg, 50-100 µg, 80-120 µg, 40-120 µg, 40-150 µg, 50-150 µg, 50-200 µg, 80-200 µg, 100-200 µg, 120-250 µg, 150-250 µg, 180-280 µg, 200-300 µg, 50-300 µg, 80-300 µg, 100-300 µg, 40-300 µg, 50-350 µg, 100-350 µg, 200-350 µg, 300-350 µg, 320-400 µg, 40-380 µg, 40-100 µg, 100-400 µg, 200-400 µg, or 300-400 µg per dose.

In some embodiments, a dosage of 25 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 100 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 50 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 75 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 150 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 400 micrograms of the mRNA (e.g., mRNA encoding infectious disease antigen, encoding PADRE, or encoding both the infectious disease antigen and PADRE) is included in the nucleic acid vaccine administered to the subject. In some embodiments, a dosage of 200 micrograms of the mRNA (e.g., mRNA encoding infectious disease antigen, encoding PADRE, or encoding both the infectious disease antigen and PADRE) is included in the nucleic acid vaccine administered to the subject. In some embodiments, the mRNA accumulates at a 100 fold higher level in the local lymph node in comparison with the distal lymph node. In some embodiments, the nucleic acid vaccine is chemically modified, and in other embodiments the nucleic acid vaccine is not chemically modified.

In some embodiments, the effective amount is a total dose of 1-100 µg. In some embodiments, the effective amount is a total dose of 100 µg. In some embodiments, the effective amount is a dose of 25 µg administered to the subject a total of one or two times. In some embodiments, the effective amount is a dose of 100 µg administered to the subject a total of two times. In some embodiments, the effective amount is a dose of 1 µg-10 µg, 1 µg-20 µg, 1 µg-30 µg, 5 µg-10 µg, 5 µg-20 µg, 5 µg-30 µg, 5 µg-40 µg, 5 µg-50 µg, 10 µg-15 µg, 10 µg-20 µg, 10 µg-25 µg, 10 µg-30 µg, 10 µg-40 µg, 10 µg-50 µg, 10 µg-60 µg, 15 µg-20 µg, 15 µg-25 µg, 15 µg-30 µg, 15 µg-40 µg, 15 µg-50 µg, 20 µg-25 µg, 20 µg-30 µg, 20 µg-40 µg, 20 µg-50 µg, 20 µg-60 µg, 20 µg-70 µg, 20 µg-75 µg, 30 µg-35 µg, 30 µg-40 µg, 30 µg-45 µg, 30 µg-50 µg, 30 µg-60 µg, 30 µg-70 µg, 30 µg-75 µg which may be administered to the subject a total of one or two times or more.

The immunogenic compositions, in some embodiments, may be used in combination with one or more pharmaceutically acceptable excipients and/or adjuvants (in addition to the PADRE).

Immunogenic compositions may be sterile, pyrogen-free or both sterile and pyrogen-free. General considerations in the formulation and/or manufacture of pharmaceutical agents, such as immunogenic compositions (e.g., vaccines), may be found, for example, in Remington: The Science and Practice of Pharmacy 21st ed., Lippincott Williams & Wilkins, 2005 (incorporated herein by reference in its entirety).

Herein, the term "active ingredient" generally refers to mRNA encoding an antigen and/or PADRE of the immunogenic compositions. By way of example, an immunogenic composition may comprise between 0.1% and 100%, e.g., between 0.5 and 50%, between 1-30%, between 5-80%, at least 80% (w/w) active ingredient. Relative amounts of the active ingredient, the pharmaceutically acceptable excipient, and/or any additional ingredients in an immunogenic composition in accordance with the disclosure will vary, depending upon the identity, size, and/or condition of the subject treated and further depending upon the route by which the composition is to be administered.

Immunogenic compositions can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected the mRNA (e.g., for transplantation into a subject), hyaluronidase, nanoparticle mimics and combinations thereof.

Immunogenic compositions may be prepared by any method known or hereafter developed in the art of pharmacology. In general, such preparatory methods include the step of bringing the active ingredient (e.g., mRNA) into association with an excipient and/or one or more other accessory ingredients, and then, if necessary and/or desirable, dividing, shaping and/or packaging the product into a desired single-dose or multi-dose unit.

Dosing/Administration

Provided herein are compositions (e.g., pharmaceutical compositions), methods, kits and reagents for prevention and/or treatment of infectious disease (e.g., ZIKV) in humans and other mammals, the RNA vaccines can be used as therapeutic or prophylactic agents. In some aspects, the RNA vaccines of the disclosure are used to provide prophylactic protection from an infectious disease (e.g, ZIKV). In some aspects, the RNA vaccines of the disclosure are used to treat an infection. In some embodiments, the vaccines of the present disclosure are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, the vaccines are administered to a subject (e.g., a mammalian subject, such as a human subject) in an effective amount to induce an antigen-specific immune response. The RNA encoding the antigen is expressed and translated in vivo to produce the antigen, which then stimulates an immune response in the subject.

Prophylactic protection from infectious disease (e.g., ZIKV) can be achieved following administration of an RNA vaccine of the present disclosure. Vaccines can be administered once, twice, three times, four times or more but it is likely sufficient to administer the vaccine once (optionally followed by a single booster). It is possible, although less desirable, to administer the vaccine to an infected individual to achieve a therapeutic response. Dosing may need to be adjusted accordingly.

A method of eliciting an immune response in a subject against infectious disease (e.g., ZIKV) is provided in aspects of the present disclosure. The method involves administering to the subject an RNA vaccine comprising at least one RNA (e.g., mRNA) having an open reading frame encoding at least one antigen, thereby inducing in the subject an immune response specific to the antigen, wherein anti-antigen antibody titer in the subject is increased following vaccination relative to anti-antigen antibody titer in a subject vaccinated with a prophylactically effective dose of a traditional vaccine against the pathogen. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the pathogen or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the pathogen or an unvaccinated subject.

A method of eliciting an immune response in a subject against an infectious disease (e.g., ZIKV) is provided in other aspects of the disclosure. The method involves administering to the subject the RNA vaccine comprising at least one RNA polynucleotide having an open reading frame encoding at least one infectious disease (e.g., ZIKV) antigen, thereby inducing in the subject an immune response specific to the antigen, wherein the immune response in the subject is equivalent to an immune response in a subject vaccinated with a traditional vaccine against the infectious disease (e.g., ZIKV) at 2 times to 100 times the dosage level relative to the RNA vaccine.

In some embodiments, the immune response in the subject is equivalent to an immune response in a subject vaccinated with a traditional vaccine at twice the dosage level relative to the RNA vaccine. In some embodiments, the immune response in the subject is equivalent to an immune response in a subject vaccinated with a traditional vaccine at three times the dosage level relative to the RNA vaccine. In some embodiments, the immune response in the subject is equivalent to an immune response in a subject vaccinated with a traditional vaccine at 4 times, 5 times, 10 times, 50 times, or 100 times the dosage level relative to the RNA vaccine. In some embodiments, the immune response in the subject is equivalent to an immune response in a subject vaccinated with a traditional vaccine at 10 times to 1000 times the dosage level relative to the RNA vaccine. In some embodiments, the immune response in the subject is equivalent to an immune response in a subject vaccinated with a traditional vaccine at 100 times to 1000 times the dosage level relative to the RNA vaccine.

In other embodiments, the immune response is assessed by determining [protein]antibody titer in the subject. In other embodiments, the ability of serum or antibody from an immunized subject is tested for its ability to neutralize viral uptake or reduce viral transformation of human B lymphocytes. In other embodiments, the ability to promote a robust T cell response(s) is measured using art recognized techniques.

Other aspects the disclosure provide methods of eliciting an immune response in a subject against an infectious disease (e.g., ZIKV) by administering to the subject an RNA vaccine comprising at least one RNA polynucleotide having an open reading frame encoding at least one antigen, thereby inducing in the subject an immune response specific to the antigen, wherein the immune response in the subject is induced 2 days to 10 weeks earlier relative to an immune response induced in a subject vaccinated with a prophylactically effective dose of a traditional vaccine against the pathogen. In some embodiments, the immune response in the subject is induced in a subject vaccinated with a prophylactically effective dose of a traditional vaccine at 2 times to 100 times the dosage level relative to the vaccine.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against an infectious disease (e.g., ZIKV) by administering to the subject an RNA vaccine having an open reading frame encoding a first antigen, wherein the RNA polynucleotide does not include a stabilization element, and wherein an adjuvant is not co-formulated or co-administered with the vaccine.

The RNA (e.g., mRNA) vaccines may be administered by any route which results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The RNA (e.g., mRNA) vaccines compositions are typically formulated in dosage unit form for ease of administration and uniformity of dosage. It will be understood, however, that the total daily usage of the RNA (e.g., mRNA) vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of a vaccine, as provided herein, may be as low as 20 µg, administered for example as a single dose or as two 10 µg doses. In some embodiments, the effective amount is a total dose of 20 µg-200 µg. For example, the effective amount may be a total dose of 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg. In some embodiments, the effective amount is a total dose of 25 µg-200 µg. In some embodiments, the effective amount is a total dose of 50 µg-200 µg.

In some embodiments, the RNA (e.g., mRNA) vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No. WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, the RNA (e.g., mRNA) vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, the RNA (e.g., mRNA) vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an RNA (e.g., mRNA) vaccine composition may be administered three or four times.

In some embodiments, the RNA (e.g., mRNA) vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RNA (e.g., mRNA) vaccine for use in a method of vaccinating a subject is administered the subject a single dosage of between 10 µg/kg and 400 µg/kg of the nucleic acid vaccine in an effective amount to vaccinate the subject. In some embodiments, the RNA vaccine for use in a method of vaccinating a subject is administered the subject a single dosage of between 10 µg and 400 µg of the nucleic acid vaccine in an effective amount to vaccinate the subject. In some embodiments, an RNA (e.g., mRNA) vaccine for use in a method of vaccinating a subject is administered to the subject as a single dosage of 25-1000 µg (e.g., a single dosage of mRNA encoding an antigen). In some embodiments, an RNA vaccine is administered to the subject as a single dosage of 25, 50, 100, 150, 200, 250, 300, 350, 400, 450, 500, 550, 600, 650, 700, 750, 800, 850, 900, 950 or 1000 µg. For example, an RNA vaccine may be administered to a subject as a single dose of 25-100, 25-500, 50-100, 50-500, 50-1000, 100-500, 100-1000, 250-500, 250-1000, or 500-1000 µg. In some embodiments, an RNA (e.g., mRNA) vaccine for use in a method of vaccinating a subject is administered to the subject as two dosages, the combination of which equals 25-1000 µg of the RNA (e.g., mRNA) vaccine.

An RNA (e.g., mRNA) vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Methods of Treatment/Vaccination

Provided herein are methods of using the immunogenic compositions (e.g., mRNA vaccines) for prevention and/or treatment of an infectious disease (e.g., Zika virus). The immunogenic compositions can be used as therapeutic or prophylactic agents, alone or in combination with other vaccine(s). They may be used in medicine to prevent and/or treat an infectious disease. In some embodiments, the immunogenic compositions of the present disclosure are used to provide prophylactic protection from an infectious disease. Prophylactic protection can be achieved following administration of an immunogenic compositions of the present disclosure. Immunogenic compositions may be used to treat or prevent "co-infections" containing two or more viral, bacterial and/or parasitic infections. Immunogenic compositions can be administered once, twice, three times, four times or more, but it is likely sufficient to administer the composition once (optionally followed by a single booster). It is possible, although less desirable, to administer the composition to an infected individual to achieve a therapeutic response. Dosing may need to be adjusted accordingly.

Immunogenic compositions (e.g., mRNA vaccines) may be utilized in various settings depending on the prevalence of the infection or the degree or level of unmet medical need. As a non-limiting example, immunogenic compositions may be utilized to treat and/or prevent a variety of infectious diseases. Immunogenic compositions (e.g., mRNA vaccines) of the present disclosure have superior properties in that they produce much larger antibody titers and produce responses early than commercially available anti-viral/anti-bacterial agents/compositions.

A subject may be a mammalian subject, such as a human subject. In some embodiments, a subject is an elderly human subject (e.g., an individual that is at least 65 years of age). For example, an elderly human subject may be 65, 66, 67, 68, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 years of age or older. In some embodiments, a subject is a child (e.g., an individual that is 5 years of age or younger). For example, a child may be 5, 4, 3, 2, 1 years of age or younger. In some embodiments, a child may be 6-12 months of age. For example, a child may be 6-7, 6-8, 6-9, 6-10, 6-11, 6-12, 7-8, 7-9, 7-10, 7-11, 7-12, 8-9, 8-10, 8-11, 8-12, 9-10, 9-11, 9-12, 10-11, 10-12, or 11-12 months of age. In some embodiments, a child may be 6 months, 7 months, 8 months, 9 months, 10 months, 11 months, or 12 months of age. In some embodiments, a subject is immunocompromised.

In some embodiments, an immunogenic composition capable of eliciting an immune response is administered intramuscularly and includes a compound according to Formula (I), (IA), (II), (IIa), (IIb), (IIc), (IId) or (IIe) (e.g., Compound 3, 18, 20, 25, 26, 29, 30, 60, 108-112, or 122).

A method of eliciting an immune response in a subject against an infectious disease is provided in aspects of the present disclosure. In some embodiments, the method involves administering to the subject an effective amount of an immunogenic composition (e.g., mRNA vaccine) to induce in the subject an immune response specific to an infectious disease antigen, wherein antibody titer of antibodies against an infectious disease antigen in the subject is increased following administration of the immunogenic composition relative to antibody titer in a subject vaccinated with a prophylactically effective dose of a traditional vaccine against the infectious disease.

In some embodiments, the antigen-specific immune response is characterized by measuring an anti-antigen antibody titer produced in a subject administered an immunogenic composition (e.g., mRNA vaccine) as provided herein. An antibody titer is a measurement of the amount of antibodies within a subject, for example, antibodies that are specific to a particular antigen (e.g., an anti-ZIKV F protein) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the immunogenic composition (e.g., mRNA vaccine).

In some embodiments, an antibody induced by an immunogenic composition is a neutralizing antibody against the infectious disease antigen. A neutralizing titer is produced by a neutralizing antibody against a viral, bacterial or parasitic antigen, for example, as measured in serum of the subject. In some embodiments, an effective dose of the immunogenic composition is sufficient to produce more than a 500 neutralization titer. For example, an effective dose of the immunogenic composition is sufficient to produce a 1000-10,000 neutralization titer. In some embodiments, an effective dose of the immunogenic composition is sufficient to produce a 1000-2000, 1000-3000, 1000-4000, 1000-5000, 1000-6000, 1000-7000, 1000-8000, 1000-9000, 1000-10,000, 2000-3000, 2000-4000, 2000-5000, 2000-6000, 2000-7000, 2000-8000, 2000-9000, 2000-10,000, 3000-4000, 3000-5000, 3000-6000, 3000-7000, 3000-8000, 3000-9000, 3000-10,000, 4000-5000, 4000-6000, 4000-7000, 4000-8000, 4000-9000, 4000-10,000, 5000-6000, 5000-7000, 5000-8000, 5000-9000, 5000-10,000, 6000-7000, 6000-8000, 6000-9000, 6000-10,000, 7000-8000, 7000-9000, 7000-10,000, 8000-9000, 8000-10,000, or a 9000-10,000 neutralization titer. In some embodiments, an effective dose of the immunogenic composition is sufficient to produce a 500, 1000, 1500, 2000, 2500, 3000, 3500, 4000, 4500, 5000, 5500, 6000, 6500, 7000, 7500, 8000, 8500, 9000, 9500, 10,000, 11000, 12,000, 13,000, 14,000, 15,000, 16,000, 17,000, 18,000, 19000, 20,000 or higher neutralizing titer. In some embodiments, neutralizing titer is produced 1-72 hours post administration. For example, neutralizing titers may be produced 1-10, 1-20, 1-30, 1-40, 1-50, 1-60, 1-70, 1-72, 10-20, 10-30, 10-40, 10-50, 10-60, 10-70, 10-72, 20-30, 20-40, 20-50, 20-60, 20-70, 20-72, 30-40, 30-50, 30-60, 30-70, 30-72, 40-50, 40-60, 40-70, 40-72, 50-60, 50-70, 50-72, 60-70, 60-72, or 70-72 hours post administration. In some embodiments, neutralizing titers may be produced 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 56, 47, 48, 49, 50, 51, 52, 53, 54, 55, 56, 57, 58, 59, 60, 61, 62, 63, 64, 65, 66, 67, 68, 69, 70, 71, or 72 hours post administration.

In some embodiments, the anti-antigen antibody titer in the subject is increased 1 log to 10 log following administration of the immunogenic composition relative to anti-antigen antibody titer in a subject vaccinated with a prophylactically effective dose of a traditional vaccine against the antigen. In some embodiments, the anti-antigen antibody titer in the subject is increased 1 log, 2 log, 3 log, 5 log or 10 log following administration of the immunogenic composition relative to anti-antigen antibody titer in a subject vaccinated with a prophylactically effective dose of a traditional vaccine against the antigen.

In some embodiments, the anti-antigen antibody titer produced in a subject is increased at least 2 times relative to a control. For example, the anti-antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-antigen antibody titer produced in the subject is increased 2, 3, 4, 5, 6, 7, 8, 9, or 10 times relative to a control. In some embodiments, the anti-antigen antibody titer produced in a subject is increased 2-10 times relative to a control. For example, the anti-antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-antigen antibody titer produced in a subject who has not been administered immunogenic composition of the present disclosure. In some embodiments, a control is the anti-antigen antibody titer produced in a subject who has been administered a live attenuated viral vaccine. An attenuated vaccine is a vaccine produced by reducing the virulence of a viable (live). An attenuated virus is altered in a manner that renders it harmless or less virulent relative to live, unmodified virus. In some embodiments, a control is an anti-antigen antibody titer produced in a subject administered inactivated viral vaccine. In some embodiments, a control is an anti-antigen antibody titer produced in a subject administered a recombinant or purified protein vaccine. Recombinant protein vaccines typically include protein antigens that either have been produced in a heterologous expression system (e.g, bacteria or yeast) or purified from large amounts of the pathogenic organism. In some embodiments, a control is an antibody titer produced in a subject who has been administered a virus-like particle (VLP) vaccine.

In some embodiments, the method involves administering to the subject an effective amount of an immunogenic composition (e.g., mRNA vaccine) to induce in the subject an immune response specific to an infectious disease, wherein the immune response in the subject is equivalent to an immune response in a subject vaccinated with a traditional vaccine against the infectious disease antigen at 2 times to 100 times the dosage level relative to the immunogenic composition. In some embodiments, the immune response in the subject is equivalent to an immune response in a subject vaccinated with a traditional vaccine at 2, 3, 4, 5, 10, 50, 100 times the dosage level relative to the immunogenic composition (e.g., mRNA vaccine). In some embodiments, the immune response in the subject is equivalent to an immune response in a subject vaccinated with a traditional vaccine at 10-100 times, or 100-1000 times, the dosage level relative to the immunogenic composition (e.g., mRNA vaccine). In some embodiments, the immune response is assessed by determining [protein] antibody titer in the subject.

In some embodiments, the immune response in the subject is induced 2 days earlier, or 3 days earlier, relative to an immune response induced in a subject vaccinated with a prophylactically effective dose of a traditional vaccine. In some embodiments, the immune response in the subject is induced 1 week, 2 weeks, 3 weeks, 5 weeks, or 10 weeks earlier relative to an immune response induced in a subject vaccinated with a prophylactically effective dose of a traditional vaccine.

In some embodiments, the method involves administering to the subject an effective amount of an immunogenic composition (e.g., mRNA vaccine) to produce an anti-antigen antibody titer equivalent to an anti-antigen antibody titer produced in a control subject administered a standard of care dose of a recombinant or purified protein vaccine or a live attenuated or inactivated viral vaccine.

In some embodiments, an effective amount of an immunogenic composition (e.g., mRNA vaccine) is a dose equivalent to an at least 2-fold reduction in a standard of care dose of a recombinant or purified protein vaccine. For example, an effective amount of an immunogenic composition may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified protein vaccine. In some embodiments, an effective amount of an immunogenic composition is a dose equivalent to an at least at least 100-fold, at least 500-fold, or at least 1000-fold reduction in a standard of care dose of a recombinant or purified protein vaccine. In some embodiments, an effective amount of an immunogenic composition is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified protein vaccine.

In some embodiments, the anti-antigen antibody titer produced in a subject administered an effective amount of an immunogenic composition (e.g., mRNA vaccine) is equivalent to an anti-antigen antibody titer produced in a control subject administered the standard of care dose of a recombinant or protein vaccine, or a live attenuated or inactivated viral vaccine. In some embodiments, an effective amount of an immunogenic composition is a dose equivalent to a 2-fold to 1000-fold (e.g., 2-fold to 100-fold, 10-fold to 1000-fold) reduction in the standard of care dose of a recombinant or purified protein vaccine, wherein the anti-antigen antibody titer produced in the subject is equivalent to an anti-antigen antibody titer produced in a control subject administered the standard of care dose of a recombinant or purified protein vaccine, or a live attenuated or inactivated viral vaccine.

In some embodiments, an effective dose of an immunogenic composition (e.g., mRNA vaccine) described herein is sufficient to produce detectable levels of viral, bacterial or parasitic as measured in serum of the subject at 1-72 hours post administration. For example, antigen may be detected at 1, 2, 3, 4, 5, 6, 7, 8, 9, 10, 15, 20, 25, 30, 35, 40, 45, 50, 55, 60, 65, 70, or 72 hours post administration. In some embodiments, the cut off index of the antigen is 1-2 (e.g., 1, 1.5, or 2). In some embodiments, wherein the effective dose is sufficient to produce a 1,000-10,000 neutralization titer produced by neutralizing antibody against antigen as measured in serum of the subject at 1-72 hours post administration. In some embodiments, the cut-off index of antigen is 1-2.

Vaccine Efficacy

Some aspects of the present disclosure provide formulations of the RNA (e.g., mRNA) vaccine, wherein the RNA vaccine is formulated in an effective amount to produce an antigen specific immune response in a subject (e.g., production of antibodies specific to an antigen). "An effective amount" is a dose of an RNA (e.g., mRNA) vaccine effective to produce an antigen-specific immune response. Also provided herein are methods of inducing an antigen-specific immune response in a subject.

As used herein, an immune response to a vaccine or LNP of the present invention is the development in a subject of a humoral and/or a cellular immune response to a (one or more) protein(s) present in the vaccine. For purposes of the present invention, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function, and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from $CD4^+$ and $CD8^+$ T-cells.

In some embodiments, the antigen-specific immune response is characterized by measuring an anti-antigen antibody titer produced in a subject administered an RNA (e.g., mRNA) vaccine as provided herein. An antibody titer is a measurement of the amount of antibodies within a subject, for example, antibodies that are specific to a particular antigen (e.g., an anti-antigen) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the RNA (e.g., mRNA) vaccine.

In some embodiments, an anti-antigen antibody titer produced in a subject is increased by at least 1 log relative to a control. For example, anti-antigen antibody titer produced in a subject may be increased by at least 1.5, at least 2, at least 2.5, or at least 3 log relative to a control. In some embodiments, the anti-antigen antibody titer produced in the subject is increased by 1, 1.5, 2, 2.5 or 3 log relative to a control. In some embodiments, the anti-antigen antibody titer produced in the subject is increased by 1-3 log relative to a control. For example, the anti-antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-antigen antibody titer produced in a subject is increased at least 2 times relative to a control. For example, the anti-antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-antigen antibody titer produced in the subject is increased 2, 3, 4, 5, 6, 7, 8, 9, or 10 times relative to a control. In some embodiments, the anti-antigen antibody titer produced in a subject is increased 2-10 times relative to a control. For example, the anti-antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-antigen antibody titer produced in a subject who has not been administered an RNA (e.g., mRNA) vaccine. In some embodiments, a control is an anti-antigen antibody titer produced in a subject administered a recombinant or purified protein vaccine. Recombinant protein vaccines typically include protein antigens that either have been produced in a heterologous expression system (e.g., bacteria or yeast) or purified from large amounts of the pathogenic organism.

In some embodiments, the ability of a vaccine to be effective is measured in a murine model. For example, the vaccines may be administered to a murine model and the murine model assayed for induction of neutralizing antibody titers. Viral challenge studies may also be used to assess the efficacy of a vaccine of the present disclosure. For example, the vaccines may be administered to a murine model, the murine model challenged with the pathogen (e.g., ZIKV) and the murine model assayed for survival and/or immune response (e.g., neutralizing antibody response, T cell response (e.g., cytokine response)).

In some embodiments, an effective amount of an RNA (e.g., mRNA) vaccine is a dose that is reduced compared to the standard of care dose of a recombinant protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified protein vaccine, or a live attenuated or inactivated vaccine, or a VLP vaccine, that a physician/clinician or other medical professional would administer to a subject to treat or prevent, or an infectious disease-related condition, while following the standard of care guideline for treating or preventing infectious disease (e.g., ZIKV), or related condition.

In some embodiments, the anti-antigen antibody titer produced in a subject administered an effective amount of an RNA vaccine is equivalent to an anti-antigen antibody titer produced in a control subject administered a standard of care dose of a recombinant or purified protein vaccine, or a live attenuated or inactivated vaccine, or an VLP vaccine.

In some embodiments, an effective amount of an RNA (e.g., mRNA) vaccine is a dose equivalent to an at least 2-fold reduction in a standard of care dose of a recombinant or purified protein vaccine. For example, an effective amount of an RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified protein vaccine. In some embodiments, an effective amount of an RNA vaccine is a dose equivalent to an at least at least 100-fold, at least 500-fold, or at least 1000-fold reduction in a standard of care dose of a recombinant or purified protein vaccine. In some embodiments, an effective amount of an RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified protein vaccine. In some embodiments, the anti-antigen antibody titer produced in a subject administered an effective amount of an RNA vaccine is equivalent to an anti-antigen antibody titer produced in a control subject administered the standard of care dose of a recombinant or protein vaccine, or a live attenuated or inactivated vaccine, or an VLP vaccine. In some embodiments, an effective amount of an RNA (e.g., mRNA) vaccine is a dose equivalent to a 2-fold to 1000-fold (e.g., 2-fold to 100-fold, 10-fold to 1000-fold) reduction in the standard of care dose of a recombinant or purified protein vaccine, wherein the anti-antigen antibody titer produced in the subject is equivalent to an anti-antigen antibody titer produced in a control subject administered the standard of care dose of a recombinant or purified protein vaccine, or a live attenuated or inactivated vaccine, or an VLP vaccine.

In some embodiments, the effective amount of an RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 300-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 300-, 4 to 200-, 4 to 100-, 4 to 90-, 4 to 80-, 4 to 70-, 4 to 60-, 4 to 50, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900) to 1000-fold reduction in the standard of care dose of a recombinant protein vaccine. In some embodiments, such as the foregoing, the anti-antigen antibody titer produced in the subject is equivalent to an anti-antigen antibody titer produced in a control subject administered the standard of care dose of a recombinant or purified protein vaccine, or a live attenuated or inactivated vaccine, or an VLP vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 180-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 570-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820--, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant protein vaccine. In some embodiments, such as the foregoing, an anti-antigen antibody titer produced in the subject is equivalent to an anti-antigen antibody titer produced in a control subject administered the standard of care dose of a recombinant or purified protein vaccine, or a live attenuated or inactivated vaccine, or an VLP vaccine.

In some embodiments, the effective amount of an RNA (e.g., mRNA) vaccine is a total dose of 50-1000 g. In some embodiments, the effective amount of an RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400), 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 µg. In some embodiments, the effective amount of an RNA (e.g., mRNA) vaccine is a total dose of 50, 100, 150, 200, 250, 300, 350, 400, 450, 500, 550, 600, 650, 700, 750, 800, 850, 900, 950 or 1000 µg. In some embodiments, the effective amount is a dose of 25-500 µg administered to the subject a total of two times. In some embodiments, the effective amount of an RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 µg administered to the subject a total of two times. In some embodiments, the effective amount of an RNA (e.g., mRNA) vaccine is a total dose of 25, 50, 100, 150, 200, 250, 300, 350, 400, 450, or 500 µg administered to the subject a total of two times. Vaccine efficacy may be assessed using standard analyses (see, e.g., Weinberg et al., J Infect Dis. 2010 Jun. 1;201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1;201(11): 1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, efficacy of the vaccine is at least 60% relative to unvaccinated control subjects. For example, efficacy of the vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a vaccine of the present disclosure is sufficient to provide sterilizing immunity in the subject for at least 1 year. For example, the effective amount of a vaccine of the present disclosure is sufficient to provide sterilizing immunity in the subject for at least 2 years, at least 3 years, at least 4 years, or at least 5 years. In some embodiments, the effective amount of a vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a vaccine of the present disclosure is sufficient to produce detectable levels of antigen as measured in serum of the subject at 1-72 hours post administration.

Titer. An antibody titer is a measurement of the amount of antibodies within a subject, for example, antibodies that are specific to a particular antigen (e.g., an anti-antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of a vaccine of the present disclosure is sufficient to produce a 1,000-10,000 neutralizing antibody titer produced by neutralizing antibody against the antigen as measured in serum of the subject at 1-72 hours post administration. In some embodiments, the effective amount is sufficient to produce a 1,000-5,000 neutralizing antibody titer produced by neutralizing antibody against the antigen as measured in serum of the subject at 1-72 hours post administration. In some embodiments, the effective amount is sufficient to produce a 5,000-10,000 neutralizing antibody titer produced by neutralizing antibody against the antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-antigen antibody titer produced in the subject is increased by at least 1 log relative to a control. For example, an anti-antigen antibody titer produced in the subject may be increased by at least 2, 3, 4, 5, 6, 7, 8, 9 or 10 log relative to a control.

In some embodiments, an anti-antigen antibody titer produced in the subject is increased at least 2 times relative to a control. For example, an anti-antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated vaccine, an inactivated vaccine, or a protein subunit vaccine.

In some embodiments, the immunogenic composition immunizes the subject against infection for up to 2 years (e.g., 6 months, 12 months, 18 months, or 24 months). In some embodiments the immunogenic composition immunizes the subject against infection for more than 2 years (e.g., 3, 4, 5, 6, 7, 8, 9, 10 years or more).

In some embodiments, the antigen-specific immune response comprises a B cell response. In some embodiments, the antigen-specific immune response comprises a T cell response.

In some embodiments, the antigen-specific immune response comprises a PADRE-specific $CD4^+$ T cell response. A PADRE-specific $CD4^+$ T cell response may be an increase in an antigen-specific immune response in a subject administered an immunogenic composition of the present disclosure (comprising mRNA encoding PADRE), relative to an antigen-specific immune response (to the same antigen) in the absence of PADRE. The level of an antigen-specific immune response may be assessed by measuring levels of B cell activation, antibody production, cytotoxic T cell activation or helper T cell activation, for example.

In some embodiments, the antigen-specific immune response is 0.1 to 10 times stronger than an antigen-specific immune response induced in a subject administered a control immunogenic composition without an mRNA encoding a PADRE. In some embodiments, the antigen-specific immune response is 0.1, 0.2, 0.3, 0.4, 0.5, 0.6, 0.7, 0.8, 0.9, 1, 2, 3, 4, 5, 6, 7, 8, 9, or 10 times stronger. In some embodiments, the antigen-specific immune response is at least 2 times stronger than an antigen-specific immune response induced in a subject administered a control immunogenic composition without an mRNA encoding a PADRE. In some embodiments, the antigen-specific immune response is at least 5 times stronger than an antigen-specific immune response induced in a subject administered a control immunogenic composition without an mRNA encoding a PADRE. In some embodiments, the antigen-specific immune response is at least 10 times stronger than an antigen-specific immune response induced in a subject administered a control immunogenic composition without an mRNA encoding a PADRE.

Immunogenic compositions described herein may be administered by any route which results in a therapeutically effective outcome. These include, but are not limited to, intradermal, intramuscular, and/or subcutaneous administration. Immunogenic compositions described herein can be formulated into a dosage form described herein, such as an intranasal, intratracheal, or injectable (e.g., intravenous, intraocular, intravitreal, intramuscular, intradermal, intracardiac, intraperitoneal, and subcutaneous). In some embodiments, immunogenic compositions may be administered intramuscularly or intradermally, similarly to the administration of inactivated vaccines known in the art. Other modes of administration are encompassed by the present disclosure.

Immunogenic compositions may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 4) years, 45 years, 50 years, 55 years, 60 years, 65 years, 70 years, 75 years, 80 years, 85 years, 90 years, 95 years or more than 99 years. In some embodiments, the time of administration between the initial administration of the prophylactic composition and the booster may be, but is not limited to, 1 week, 2 weeks, 3 weeks, 1 month, 2 months, 3 months, 6 months or 1 year.

The exact amount of an immunogenic composition (e.g., mRNA vaccine) required will vary from subject to subject, depending on the species, age, and general condition of the subject, the severity of the disease, the particular composition, its mode of administration, its mode of activity, and the like. Immunogenic compositions are typically formulated in dosage unit form for ease of administration and uniformity of dosage. It will be understood, however, that the total daily usage of the immunogenic compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, the immunogenic compositions may be administered at dosage levels sufficient to deliver the active (e.g., mRNA) at 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see, e.g., the range of unit doses described in International Publication No WO2013078199, the contents of which are herein incorporated by reference in their entirety). The desired dosage may be delivered three times a day, two times a day, once a day, every other day, every third day, every week, every two weeks, every three weeks, every four weeks, every 2 months, every three months, every 6 months, etc. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In some embodiments, immunogenic compositions (e.g., mRNA vaccines) may be administered at dosage levels sufficient to deliver the active (e.g., mRNA) at 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, immunogenic compositions may be administered once or twice (or more) at dosage levels sufficient to deliver the active (e.g., mRNA) at 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, immunogenic compositions (e.g., mRNA vaccines) may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an immunogenic composition (e.g., mRNA vaccine) may be administered three or four times.

In some embodiments, the immunogenic compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, an immunogenic compositions for use in a method of vaccinating a subject is administered to the subject as a single dosage of between 10 µg/kg and 400 µg/kg of the mRNA (in an effective amount to vaccinate the subject). In some embodiments the immunogenic composition for use in a method of vaccinating a subject is administered to the subject as a single dosage of between 10 µg and 400 µg of the mRNA (in an effective amount to vaccinate the subject).

In some embodiments, an immunogenic composition for use in a method of vaccinating a subject is administered to the subject as a single dosage of 2-1000 µg (e.g., a single dosage of mRNA encoding antigen and/or PADRE). In some embodiments, an immunogenic composition for use in a method of vaccinating a subject is administered to the subject as a single dosage of 5-100 µg (e.g., a single dosage of mRNA encoding antigen and/or PADRE). In some embodiments, an immunogenic composition is administered to the subject as a single dosage of 2, 5, 10, 15, 20, 25, 50, 100, 150, 200, 250, 300, 350, 400, 450, 500, 550, 600, 650, 700, 750, 800, 850, 900, 950 or 1000 µg. For example, an immunogenic composition may be administered to a subject as a single dose of 5-100, 10-100, 15-100, 20-100, 25-100, 25-500, 50-100, 50-500, 50-1000, 100-500, 100-1000, 250-500, 250-1000, or 500-1000 µg. In some embodiments, an immunogenic composition for use in a method of vaccinating a subject is administered to the subject as two dosages, the combination of which equals 10-1000 µg of the mRNA encoding antigen and/or PADRE.

EXAMPLES

Example 1

An mRNA Vaccine Platform for ZIKV

A vaccine platform is developed for generating multiple lipid nanoparticles that encapsulate modified mRNA for intramuscular delivery to induce high levels of protein expression in vivo. The flexibility of platform allows for the inclusion of multiple mRNA encoding any flavivirus proteins (e.g., NS1, prME) that could augment protective responses (Costa et al., 2007; Costa et al., 2006), or immunodominant helper CD4 T cell epitopes (e.g., a PARDE epitope as described in Hung et al., 2007, Mol Ther. 2007 June; 15(6): 1211-1219, incorporated herein by reference).

A modified mRNA was designed, which encodes the prM and E proteins from an Asian ZIKV strain (Mirconesia 2007, GenBank accession number EU545988 (Lanciotti et al., 2008)), which has >99% amino acid sequence identity relative to strains from the Americas. A second modified mRNA is synthesized to encode a Pan HLA-DR reactive epitope (PADRE), which is a $CD4^+$ T-helper epitope. Alternatively, a third modified mRNA is designed to encode the prM and E genes from an Asian ZIKV strain (GenBank accession number EU545988) fused to a PADRE epitope. The amino acid sequence of the PADRE epitope is AKFVAAWTLKAAA (SEQ ID NO: 1).

The modified mRNAs are designed to include a type 1 (N7mGpppAm) cap, proprietary 5' and 3' untranslated sequences, and a coding sequence for the signal sequence from human IgE. The modified mRNAs are synthesized chemically. The prM-E-encoding mRNA is packaged alone or with the PADRE-encoding mRNAs are into one lipid nanoparticle (LNP), and the mRNA encoding the prM-E-Ii-PADRE fusion is packaged into one LNP. Incubation of LNPs containing IgE signal encoding mRNA ($IgE_{sig}$-prM-E, with or without PADRE or $IgE_{sig}$-prM-E-PADRE fusion) with 293T or HeLa cells results in efficient expression and secretion of ~30 nm SVPs, as judged by electron microscopy and negative staining, Western blotting and mass spectrometry for ZIKV structural proteins in the cell supernatants.

Example 2

Vaccine Efficacy in Immunocompromised AG129 Mice

The immunogenicity and protective activity of the prM-E encoding LNPs are assessed in immunocompromised mice lacking type I and II interferon (IFN) signaling responses. Eight week-old Ifnar1−/−Ifngr−/−AG129 male and female mice are divided into seven groups, which receive an intramuscular inoculation of 2 or 10 µg of the $IgE_{sig}$-prM-E, $IgE_{sig}$-prM-E+PADRE, or $IgE_{sig}$-prM-E-PADRE fusion LNPs or 10 µg of a non-translating RNA LNP. Groups 1, 3, 5, and 7 are boosted with the same dose at 21 days after vaccination, whereas Groups 2, 4, and 6 are not boosted. At day 42 after immunization, mice are phlebotomized for serum neutralizing antibody analysis. Mice receiving the $IgE_{sig}$-prM-E+PADRE or $IgE_{sig}$-prM-E-PADRE fusion LNPs are expected to have stronger T-cell response against ZIKV than mice receiving the $IgE_{sig}$-prM-E LNPs alone. Mice receiving only a single immunization have lower neutralizing titers than mice receiving a boost dose. At 42 days after vaccination, AG129 mice are challenged with the ZIKV strain P6-740 (Malaysia, 1966). AG129 mice receiving the negative control LNP vaccine succumbed to ZIKV infection as expected (Aliota et al., 2016). Recipients of the 2 or 10 µg LNP containing any of the $IgE_{sig}$-prM-E-encoding mRNA vaccines with or without a boost are all expected to survive the infection. Weight measurements correlates with lethality, as mice receiving the $IgE_{sig}$-prM-E, $IgE_{sig}$-prM-E+PADRE, or $IgE_{sig}$-prM-E-PADRE fusion LNP vaccines are protected, whereas the negative controls lose weight beginning at approximately day 10 after challenge to the time of death.

Example 3

Vaccine Efficacy in Wild-type C57BL/6 Mice

To test the immunogenicity and efficacy of the $IgE_{sig}$-prM-E, $IgE_{sig}$-prM-E+PADRE, or $IgE_{sig}$-prM-E-PADRE fusion LNP vaccine efficacy in an immunocompetent mouse strain, 8 week-old male C57BL/6 WT mice are inoculated via intramuscular injection with 10 µg of any of the LNPs. These animals are phlebotomized prior to a single boost at day 28 (4 weeks) and before challenge at either day 56 (8 weeks) or day 126 (18 weeks). Serum neutralization titers are expected to be relatively low prior to boosting. However, titers peak at 4 weeks after boosting and remain elevated 18 weeks post initial vaccination. To create a lethal challenge model, 2 mg of a blocking anti-Ifnar1 antibody are passively transferred one day prior to infection with 10⁶ focus-forming units (FFU) of a mouse-adapted African ZIKV strain (Dakar 41519) (Sapparapu et al., 2016; Zhao et al., 2016). All mice immunized with $IgE_{sig}$-prM-E, $IgE_{sig}$-prM-E+PADRE, or $IgE_{sig}$-prM-E-PADRE fusion LNPs, are protected against lethal ZIKV infection compared to the control group, which has a less than 30% survival rate. Mice vaccinated with any of the prM-E mRNA LNPs do not display any loss in weight nor have measurable viremia in serum at 5 days after challenge.

Example 4

Modified Vaccines Lacking the Immunodominant E-DII-FL Epitope Generate a Protective Anti-ZIKV Response The highly conserved FL epitope in DII of the flavivirus E protein is immunodominant in humans (Beltramello et al., 2010; Crill et al., 2007; Dejnirattisai et al., 2010; Oliphant et al., 2007; Sapparapu et al., 2016; Stettler et al., 2016). As such, infection with ZIKV or vaccination with ZIKV structural proteins could induce cross-reactive antibodies, which might enhance DENV infection and disease through ADE (Morens, 1994; Stettler et al., 2016). To minimize this possibility, modified mRNA vaccines by engineering four mutations (T76R, Q77E, W101R, and L107R) in or near the FL ($IgE_{sig}$-prM-E-FL, $IgE_{sig}$-prM-E-FL+PADRE, and $IgE_{sig}$-prM-E-FL-PADRE fusion) are generated that abolish antibody reactivity of FL-specific antibodies (Chabierski et al., 2014; Crill et al., 2012; Oliphant et al., 2007). Thus, a separate series of mRNA LNPs as described in Example 1 (prM-E, prM-E+PADRE, prM-E-PADRE fusion, prM-E-FL, prM-E-FL+PADRE, and prM-E-FL-PADRE fusion) are generated by replacing the IgE leader sequence with one from Japanese encephalitis virus ($JEV_{sig}$), a feature included in other flavivirus prM-E DNA vaccines to increase the efficiency of host signalase cleavage (Davis et al., 2001; Dowd et al., 2016b), and by further optimizing codon usage. Western blotting analysis showed similar levels of SVP expression in HeLa cell supernatants after transfection of WT and FL mutant mRNA, and a loss of FL reactivity is confirmed for the prM-E-FL mRNAs by an absence of binding of a mAb (WNV E60) that recognizes this epitope (Oliphant et al., 2006).

Immunocompetent 8 week-old female BALB/c mice are immunized with 2 µg or 10 µg of $IgE_{sig}$-prM-E or $JEV_{sig}$-prM-E (WT or FL mutant) LNPs and boosted with the same LNPs 4 weeks later. At 8 weeks after initial vaccination, serum is analyzed for neutralizing activity using ZIKV reporter virus particles (RVPs) (Dowd et al., 2016a). Mice receiving 2 or 10 µg doses of the $IgE_{sig}$-prM-E WT and FL mutant LNPs show similar neutralization titers, with mean EC50 values of ~1/5,000. The 2 and 10 µg dose of the WT $JEV_{sig}$-prM-E LNPs induces stronger inhibitory responses with remarkable EC50 values of ~1/100,000 and EC90 values of ~1/10,000. The mutant $JEV_{sig}$-prM-E-FL LNPs, however, induces antibody responses with lower EC50 and EC90 values, which still approach 1/10,000 and 1/500, respectively. At ~13 weeks after initial vaccination, mice are challenged with ZIKV Dakar 41519 after pre-administration of anti-Ifnar1 blocking antibody. At day 3 after infection, serum is analyzed for viremia. Consistent with their high neutralizing titers, all mice immunized with 2 or 10 µg doses of $JEV_{sig}$-prM-E LNPs lack measurable viremia. All other vaccine groups ($IgE_{sig}$-prM E LNPs (WT or FL) or $JEV_{sig}$-prM-E-FL LNPs) have breakthrough viremia in some animals, although levels are 10 to 100-fold lower than observed with placebo LNPs. Mice are sacrificed at day 7 after infection and spleen, uterus, and brain are analyzed for ZIKV RNA levels. Most mice vaccinated with prM-E LNPs show markedly reduced levels of viral RNA in the spleen (>100-fold) and virtually no detectable viral RNA in the uterus or brain, whereas the placebo immunized animals have mean levels of 10⁵ to 10⁶ FFU equivalents per gram of tissue. Mice vaccinated with the 2 μg dose of IgE$_{sig}$-prM-E-FL or JEV$_{sig}$-prM-E-FL LNPs, with or without PARDE, show slightly less protection, as viral RNA is detectable in some animals in the spleen and brain albeit at much lower levels than those immunized with placebo LNPs. To begin to establish an immune correlate of complete protection against ZIKV in this model, the EC50 values from all mRNA LNP vaccines are compared with the levels of viral RNA recovered in the serum and spleen from individual mice. This analysis reveal an expected inverse relationship between neutralizing titers and levels of ZIKV RNA in serum and tissues, and establish a cut-off EC50 value of ~1/10,000 to completely prevent viremia and tissue dissemination. Next, the JEV$_{sig}$-prM-E mRNA LNP vaccines, with or without PADRE, which protect almost completely against viremia or infection in tissues, are evaluated for conferred sterilizing immunity. The vast majority of animals (80 to 90%) receiving 2 or 10 μg doses of the JEV$_{sig}$-prM-E mRNA vaccines failed to boost their neutralizing titers one week after challenge with infectious ZIKV, consistent with sterilizing immunity. In comparison, most animals (82-100%) showing breakthrough viremia or tissue burden with the IgE$_{sig}$-prM-E or JEV$_{sig}$-prM-E-FL mRNA vaccines sustain marked increases in EC50 and EC90 values after challenge, consistent with the induction of an anamnestic response.

Example 5

Mutation of the DII-fusion Loop Epitope Diminishes ADE in Cells and Mice

The FL mutant LNPs are engineered to reduce the production of cross-reactive antibodies and the possibility of immune enhancement of DENV. To evaluate whether the FL mutant LNP vaccines diminished induction of cross-reactive enhancing antibodies, dilutions of serum obtained at 8 weeks after immunization are incubated with DENV serotype 1 (DENV-1) RVPs and assessed infection in K562 cells, which express the activating human Fc-γ receptor IIA (CD32A). Whereas sera from mice vaccinated with WT IgE$_{sig}$-prM-E or JEV$_{sig}$-prM-E mRNA LNPs all show bell-shaped, canonical antibody enhancement curves, many of the sera from mice immunized with serum from IgE$_{sig}$-prM-E-FL or JEV$_{sig}$-prM-E-FL LNPs (with or without PADRE) support enhancement at only high concentrations and with considerably reduced efficiency. Indeed, the peak serum enhancement titer (PET (Boonnak et al., 2008)) is ~100-fold lower in mice immunized with mutant forms of the fusion loop. A similar reduction in enhancing power, or the relative fraction of infected cells at the PET assayed in parallel, is observed. Thus, introduction of mutations in the FL of ZIKV E reduces the production of enhancing antibodies against DENV, as judged by cell culture assays. To determine the physiological significance of these results, an established passive transfer model of ADE for DENV in AG129 mice is used with serum from the IgE$_{sig}$-prM-E and IgE$_{sig}$-prM-E-FL (with or without PADRE) vaccinated mice. First, the relative neutralizing activity of DENV-2 of pooled ZIKV serum is evaluated using an established DENV-2 RVP assay in Raji-DCSIGNR cells. Consistent with studies using FL-specific mAbs, the pooled sera from IgE$_{sig}$-prM-E but not IgE$_{sig}$-prM-E-FL vaccinated animals inhibit DENV-2 infection in cell culture, indicating a cross-reactive antibody (likely FL specific) is produced only in mice receiving any of the IgE$_{sig}$-prM-E vaccines, and this antibody can neutralize infection in Raji-DCSIGNR cells lacking activating Fc-γ receptors. Next, pooled sera are transferred to AG129 mice one day prior to challenge with a non-lethal dose of DENV-2. Whereas administration of serum from mice vaccinated with WT IgE$_{sig}$-prM-E LNPs or a positive control anti-prM mAb (2H2) results in lethal infection and severe disease due to antibody enhancement, transfer of equivalent amounts of sera from mice vaccinated with IgE$_{sig}$-prM-E-FL mutant LNPs results in no mortality and manifested only mild clinical signs of disease.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An immunogenic composition, comprising a cationic lipid nanoparticle (LNP) encapsulating messenger ribonucleic acid (mRNA) having an open reading frame encoding a Zika Virus (ZIKV) prM antigen, a ZIKV E antigen, and a pan HLA DR-binding epitope (PADRE), and a 5' terminal cap wherein the cationic lipid nanoparticle comprises a cationic lipid, a PEG-modified lipid, a sterol, and a non-cationic lipid.

2. An immunogenic composition, comprising a cationic lipid nanoparticle (LNP) encapsulating (a) a messenger ribonucleic acid (mRNA) having an open reading frame encoding a Zika Virus (ZIKV) prM antigen, a ZIKV E antigen, and a 5' terminal cap; and (b) a mRNA having an open reading frame encoding a pan HLA DR-binding epitope (PADRE), and a 5' terminal cap, wherein the cationic lipid nanoparticle comprises a cationic lipid, a PEG-modified lipid, a sterol and a non-cationic lipid.

3. The immunogenic composition of claim 1, wherein the ZIKV prM antigen and the ZIKV E antigen form a fusion antigen comprising a sequence identified by SEQ ID NO: 2, SEQ ID NO: 4, or SEQ ID NO: 6.

4. The immunogenic composition of claim 1, wherein the open reading frame is codon optimized.

5. The immunogenic composition of claim 1, wherein at least 80% of the uracil in the open reading frame has a chemical modification.

6. The immunogenic composition of claim 5, wherein the chemical modification is N1-methylpseudouridine or N1-ethylpseudouridine.

7. The immunogenic composition of claim 5, wherein the chemical modification is at the carbon 5-position of the uracil.

8. The immunogenic composition of claim 1, wherein the 5' terminal cap is 7mG(5')ppp(5')N1mpNp.

9. The immunogenic composition of claim 1, wherein the open reading frame of the mRNA further encodes a signal sequence.

10. The immunogenic composition of claim 9, wherein the signal sequence is the Japanese encephalitis prM signal sequence MWLVSLAIVTACAGA shown in SEQ ID NO: 11.

11. The immunogenic composition of claim 1, wherein the cationic lipid nanoparticle comprises a molar ratio of 20-60% cationic lipid, 0.5-15% PEG-modified lipid, 25-55% sterol, and 5-25% non-cationic lipid.

12. The immunogenic composition of claim 1, wherein the cationic lipid is an ionizable cationic lipid and the non-cationic lipid is a neutral lipid, and the sterol is a cholesterol.

13. The immunogenic composition of claim 1, wherein the cationic lipid nanoparticle comprises a compound of Formula (I).

14. The immunogenic composition of claim 13, wherein the cationic lipid nanoparticle comprises Compound 1 or Compound 2.

15. A method of inducing an immune response in a subject, the method comprising administering to the subject the immunogenic composition of claim 1 in an amount effective to produce an antigen-specific immune response in the subject.

16. The immunogenic composition of claim 2, wherein the ZIKV prM antigen and the ZIKV E antigen form a fusion antigen comprising a sequence identified by SEQ ID NO: 2, SEQ ID NO: 4, or SEQ ID NO: 6.

17. The immunogenic composition of claim 2, wherein the ratio of mRNA encoding ZIKV antigen to mRNA encoding PADRE is 0.1:1 to 10:1.

18. The immunogenic composition of claim 2, wherein at least one of the open reading frames is codon optimized.

19. The immunogenic composition of claim 2, wherein at least 80% of the uracil in at least one of the open reading frames has a chemical modification.

20. The immunogenic composition of claim 19, wherein the chemical modification is N1-methylpseudouridine or N1-ethylpseudouridine.

21. The immunogenic composition of claim 19, wherein the chemical modification is at the carbon 5-position of the uracil.

22. The immunogenic composition of claim 2, wherein at least one of the 5' terminal caps is 7mG(5')ppp(5')N1mpNp.

23. The immunogenic composition of claim 2, wherein at least one of the open reading frames of the mRNA further encodes a signal sequence.

24. The immunogenic composition of claim 23, wherein the signal sequence is the Japanese encephalitis prM signal sequence MWLVSLAIVTACAGA shown in SEQ ID NO: 11.

25. The immunogenic composition of claim 2, wherein the cationic lipid nanoparticle comprises a molar ratio of 20-60% cationic lipid, 0.5-15% PEG-modified lipid, 25-55% sterol, and 5-25% non-cationic lipid.

26. The immunogenic composition of claim 2, wherein the cationic lipid is an ionizable cationic lipid and the non-cationic lipid is a neutral lipid, and the sterol is a cholesterol.

27. The immunogenic composition of claim 2, wherein the cationic lipid nanoparticle comprises a compound of Formula (I).

28. The immunogenic composition of claim 27, wherein the cationic lipid nanoparticle comprises Compound 1 or Compound 2.

* * * * *

SEQUENCE LISTING

```
<160> NUMBER OF SEQ ID NOS: 14

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Ala Lys Phe Val Ala Ala Trp Thr Leu Lys Ala Ala Ala
1               5                   10

<210> SEQ ID NO 2
```

<211> LENGTH: 672
<212> TYPE: PRT
<213> ORGANISM: Zika virus

<400> SEQUENCE: 2

```
Ala Glu Val Thr Ar

```
                385                 390                 395                 400
        Thr Pro His Trp Asn Asn Lys Glu Ala Leu Val Glu Phe Lys Asp Ala
                        405                 410                 415

His Ala Lys Arg Gln Thr Val Val Leu Gly Ser Gln Glu Gly Ala
                420                 425                 430

Val His Thr Ala Leu Ala Gly Ala Leu Glu Ala Glu Met Asp Gly Ala
                        435                 440                 445

Lys Gly Arg Leu Ser Ser Gly His Leu Lys Cys Arg Leu Lys Met Asp
                450                 455                 460

Lys Leu Arg Leu Lys Gly Val Ser Tyr Ser Leu Cys Thr Ala Ala Phe
        465                 470                 475                 480

Thr Phe Thr Lys Ile Pro Ala Glu Thr Leu His Gly Thr Val Thr Val
                        485                 490                 495

Glu Val Gln Tyr Ala Gly Thr Asp Gly Pro Cys Lys Val Pro Ala Gln
                        500                 505                 510

Met Ala Val Asp Met Gln Thr Leu Thr Pro Val Gly Arg Leu Ile Thr
                515                 520                 525

Ala Asn Pro Val Ile Thr Glu Ser Thr Glu Asn Ser Lys Met Met Leu
        530                 535                 540

Glu Leu Asp Pro Pro Phe Gly Asp Ser Tyr Ile Val Ile Gly Val Gly
        545                 550                 555                 560

Glu Lys Lys Ile Thr His His Trp His Arg Ser Gly Ser Thr Ile Gly
                        565                 570                 575

Lys Ala Phe Glu Ala Thr Val Arg Gly Ala Lys Arg Met Ala Val Leu
                        580                 585                 590

Gly Asp Thr Ala Trp Asp Phe Gly Ser Val Gly Gly Ala Leu Asn Ser
                595                 600                 605

Leu Gly Lys Gly Ile His Gln Ile Phe Gly Ala Ala Phe Lys Ser Leu
                        610                 615                 620

Phe Gly Gly Met Ser Trp Phe Ser Gln Ile Leu Ile Gly Thr Leu Leu
        625                 630                 635                 640

Met Trp Leu Gly Leu Asn Thr Lys Asn Gly Ser Ile Ser Leu Met Cys
                        645                 650                 655

Leu Ala Leu Gly Gly Val Leu Ile Phe Leu Ser Thr Ala Val Ser Ala
                        660                 665                 670

<210> SEQ ID NO 3
<211> LENGTH: 687
<212> TYPE: PRT
<213> ORGANISM: Zika virus

<400> SEQUENCE: 3

Met Trp Leu Val Ser Leu Ala Ile Val Thr Ala Cys Ala Gly Ala Ala
        1               5                   10                  15

Glu Val Thr Arg Arg Gly Ser Ala Tyr Tyr Met Tyr Leu Asp Arg Asn
                        20                  25                  30

Asp Ala Gly Glu Ala Ile Ser Phe Pro Thr Thr Leu Gly Met Asn Lys
                    35                  40                  45

Cys Tyr Ile Gln Ile Met Asp Leu Gly His Met Cys Asp Ala Thr Met
                50                  55                  60

Ser Tyr Glu Cys Pro Met Leu Asp Glu Gly Val Glu Pro Asp Asp Val
        65                  70                  75                  80

Asp Cys Trp Cys Asn Thr Thr Ser Thr Trp Val Val Tyr Gly Thr Cys
                        85                  90                  95
```

-continued

```
His His Lys Lys Gly Glu Ala Arg Arg Ser Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
        130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
210                 215                 220

Asp Ile Glu Leu Val Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
        275                 280                 285

Gly Leu Phe Gly Lys Gly Ser Leu Val Thr Cys Ala Lys Phe Ala Cys
290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
        355                 360                 365

Leu Gly Leu Asp Cys Glu Pro Arg Thr Gly Leu Asp Phe Ser Asp Leu
370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
            420                 425                 430

Ala Lys Arg Gln Thr Val Val Val Leu Gly Ser Gln Glu Gly Ala Val
        435                 440                 445

His Thr Ala Leu Ala Gly Ala Leu Glu Ala Glu Met Asp Gly Ala Lys
450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
```

```
            515                 520                 525
Ala Val Asp Met Gln Thr Leu Thr Pro Val Gly Arg Leu Ile Thr Ala
    530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
    610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Met
                645                 650                 655

Trp Leu Gly Leu Asn Thr Lys Asn Gly Ser Ile Ser Leu Met Cys Leu
            660                 665                 670

Ala Leu Gly Gly Val Leu Ile Phe Leu Ser Thr Ala Val Ser Ala
        675                 680                 685

<210> SEQ ID NO 4
<211> LENGTH: 672
<212> TYPE: PRT
<213> ORGANISM: Artificial Sequence
<220> FEATURE:
<223> OTHER INFORMATION: Synthetic Polypeptide

<400> SEQUENCE: 4

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Val Val
            180                 185                 190

Leu Glu His Gly Gly Cys Val Thr Val Met Ala Gln Asp Lys Pro Thr
```

```
                195                 200                 205
Val Asp Ile Glu Leu Val Thr Thr Val Ser Asn Met Ala Glu Val
210                 215                 220

Arg Ser Tyr Cys Tyr Glu Ala Ser Ile Ser Asp Met Ala Ser Asp Ser
225                 230                 235                 240

Arg Cys Pro Arg Glu Gly Ala Tyr Leu Asp Lys Gln Ser Asp Thr
                245                 250                 255

Gln Tyr Val Cys Lys Arg Thr Leu Val Asp Arg Gly Arg Gly Asn Gly
                260                 265                 270

Cys Gly Arg Phe Gly Lys Gly Ser Leu Val Thr Cys Ala Lys Phe Ala
            275                 280                 285

Cys Ser Lys Lys Met Thr Gly Lys Ser Ile Gln Pro Glu Asn Leu Glu
290                 295                 300

Tyr Arg Ile Met Leu Ser Val His Gly Ser Gln His Ser Gly Met Ile
305                 310                 315                 320

Val Asn Asp Thr Gly His Glu Thr Asp Glu Asn Arg Ala Lys Val Glu
                325                 330                 335

Ile Thr Pro Asn Ser Pro Arg Ala Glu Ala Thr Leu Gly Gly Phe Gly
                340                 345                 350

Ser Leu Gly Leu Asp Cys Glu Pro Arg Thr Gly Leu Asp Phe Ser Asp
            355                 360                 365

Leu Tyr Tyr Leu Thr Met Asn Asn Lys His Trp Leu Val His Lys Glu
370                 375                 380

Trp Phe His Asp Ile Pro Leu Pro Trp His Ala Gly Ala Asp Thr Gly
385                 390                 395                 400

Thr Pro His Trp Asn Asn Lys Glu Ala Leu Val Glu Phe Lys Asp Ala
                405                 410                 415

His Ala Lys Arg Gln Thr Val Val Val Leu Gly Ser Gln Glu Gly Ala
                420                 425                 430

Val His Thr Ala Leu Ala Gly Ala Leu Glu Ala Glu Met Asp Gly Ala
            435                 440                 445

Lys Gly Arg Leu Ser Ser Gly His Leu Lys Cys Arg Leu Lys Met Asp
            450                 455                 460

Lys Leu Arg Leu Lys Gly Val Ser Tyr Ser Leu Cys Thr Ala Ala Phe
465                 470                 475                 480

Thr Phe Thr Lys Ile Pro Ala Glu Thr Leu His Gly Thr Val Thr Val
                485                 490                 495

Glu Val Gln Tyr Ala Gly Thr Asp Gly Pro Cys Lys Val Pro Ala Gln
                500                 505                 510

Met Ala Val Asp Met Gln Thr Leu Thr Pro Val Gly Arg Leu Ile Thr
            515                 520                 525

Ala Asn Pro Val Ile Thr Glu Ser Thr Glu Asn Ser Lys Met Met Leu
            530                 535                 540

Glu Leu Asp Pro Pro Phe Gly Asp Ser Tyr Ile Val Ile Gly Val Gly
545                 550                 555                 560

Glu Lys Lys Ile Thr His His Trp His Arg Ser Gly Ser Thr Ile Gly
                565                 570                 575

Lys Ala Phe Glu Ala Thr Val Arg Gly Ala Lys Arg Met Ala Val Leu
            580                 585                 590

Gly Asp Thr Ala Trp Asp Phe Gly Ser Val Gly Gly Ala Leu Asn Ser
            595                 600                 605

Leu Gly Lys Gly Ile His Gln Ile Phe Gly Ala Ala Phe Lys Ser Leu
            610                 615                 620
```

```
Phe Gly Gly Met Ser Trp Phe Ser Gln Ile Leu Ile Gly Thr Leu Leu
625                 630                 635                 640

Met Trp Leu Gly Leu Asn Thr Lys Asn Gly Ser Ile Ser Leu Met Cys
            645                 650                 655

Leu Ala Leu Gly Gly Val Leu Ile Phe Leu Ser Thr Ala Val Ser Ala
            660                 665                 670

<210> SEQ ID NO 5
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 5

Met Trp Leu Val Ser Leu Ala Ile Val Thr Ala Cys Ala Gly Ala Ala
1               5                   10                  15

Glu Val Thr Arg Arg Gly Ser Ala Tyr Tyr Met Tyr Leu Asp Arg Asn
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
            260                 265                 270

Tyr Val Cys Lys Arg Thr Leu Val Asp Arg Gly Arg Gly Asn Gly Cys
        275                 280                 285

Gly Arg Phe Gly Lys Gly Ser Leu Val Thr Cys Ala Lys Phe Ala Cys
290                 295                 300

Ser Lys Lys Met Thr Gly Lys Ser Ile Gln Pro Glu Asn Leu Glu Tyr
305                 310                 315                 320
```

Arg Ile Met Leu Ser Val His Gly Ser Gln His Ser Gly Met Ile Val
            325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
            355                 360                 365

Leu Gly Leu Asp Cys Glu Pro Arg Thr Gly Leu Asp Phe Ser Asp Leu
        370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
            420                 425                 430

Ala Lys Arg Gln Thr Val Val Leu Gly Ser Gln Glu Gly Ala Val
        435                 440                 445

His Thr Ala Leu Ala Gly Ala Leu Glu Ala Glu Met Asp Gly Ala Lys
    450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
        515                 520                 525

Ala Val Asp Met Gln Thr Leu Thr Pro Val Gly Arg Leu Ile Thr Ala
    530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
    610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Met
                645                 650                 655

Trp Leu Gly Leu Asn Thr Lys Asn Gly Ser Ile Ser Leu Met Cys Leu
            660                 665                 670

Ala Leu Gly Gly Val Leu Ile Phe Leu Ser Thr Ala Val Ser Ala
        675                 680                 685

<210> SEQ ID NO 6
<211> LENGTH: 690
<212> TYPE: PRT
<213> ORGANISM: Artificial Sequence
<220> FEATURE:
<223> OTHER INFORMATION: Synthetic Polypeptide

<400> SEQUENCE: 6

```
Met Asp Trp Thr Trp Ile Leu Phe Leu Val Ala Ala Thr Arg Val
1               5                   10                  15

His Ser Ala Glu Val Thr Arg Arg Gly Ser Ala Tyr Tyr Met Tyr Leu
            20                  25                  30

Asp Arg Asn Asp Ala Gly Glu Ala Ile Ser Phe Pro Thr Thr Leu Gly
            35                  40                  45

Met Asn Lys Cys Tyr Ile Gln Ile Met Asp Leu Gly His Met Cys Asp
            50                  55                  60

Ala Thr Met Ser Tyr Glu Cys Pro Met Leu Asp Glu Gly Val Glu Pro
65              70                  75                  80

Asp Asp Val Asp Cys Trp Cys Asn Thr Thr Ser Thr Trp Val Val Tyr
                85                  90                  95

Gly Thr Cys His His Lys Lys Gly Glu Ala Arg Arg Ser Arg Arg Ala
                100                 105                 110

Val Thr Leu Pro Ser His Ser Thr Arg Lys Leu Gln Thr Arg Ser Gln
                115                 120                 125

Thr Trp Leu Glu Ser Arg Glu Tyr Thr Lys His Leu Ile Arg Val Glu
        130                 135                 140

Asn Trp Ile Phe Arg Asn Pro Gly Phe Ala Leu Ala Ala Ala Ala Ile
145                 150                 155                 160

Ala Trp Leu Leu Gly Ser Ser Thr Ser Gln Lys Val Ile Tyr Leu Val
                165                 170                 175

Met Ile Leu Leu Ile Ala Pro Ala Tyr Ser Ile Arg Cys Ile Gly Val
                180                 185                 190

Ser Asn Arg Asp Phe Val Glu Gly Met Ser Gly Gly Thr Trp Val Asp
        195                 200                 205

Val Val Leu Glu His Gly Gly Cys Val Thr Val Met Ala Gln Asp Lys
        210                 215                 220

Pro Thr Val Asp Ile Glu Leu Val Thr Thr Thr Val Ser Asn Met Ala
225                 230                 235                 240

Glu Val Arg Ser Tyr Cys Tyr Glu Ala Ser Ile Ser Asp Met Ala Ser
                245                 250                 255

Asp Ser Arg Cys Pro Arg Glu Gly Glu Ala Tyr Leu Asp Lys Gln Ser
                260                 265                 270

Asp Thr Gln Tyr Val Cys Lys Arg Thr Leu Val Asp Arg Gly Arg Gly
        275                 280                 285

Asn Gly Cys Gly Arg Phe Gly Lys Gly Ser Leu Val Thr Cys Ala Lys
        290                 295                 300

Phe Ala Cys Ser Lys Lys Met Thr Gly Lys Ser Ile Gln Pro Glu Asn
305                 310                 315                 320

Leu Glu Tyr Arg Ile Met Leu Ser Val His Gly Ser Gln His Ser Gly
                325                 330                 335

Met Ile Val Asn Asp Thr Gly His Glu Thr Asp Glu Asn Arg Ala Lys
                340                 345                 350

Val Glu Ile Thr Pro Asn Ser Pro Arg Ala Glu Ala Thr Leu Gly Gly
        355                 360                 365

Phe Gly Ser Leu Gly Leu Asp Cys Glu Pro Arg Thr Gly Leu Asp Phe
370                 375                 380

Ser Asp Leu Tyr Tyr Leu Thr Met Asn Asn Lys His Trp Leu Val His
385                 390                 395                 400

Lys Glu Trp Phe His Asp Ile Pro Leu Pro Trp His Ala Gly Ala Asp
                405                 410                 415
```

Thr Gly Thr Pro His Trp Asn Asn Lys Glu Ala Leu Val Glu Phe Lys
            420                 425                 430

Asp Ala His Ala Lys Arg Gln Thr Val Val Leu Gly Ser Gln Glu
        435                 440                 445

Gly Ala Val His Thr Ala Leu Ala Gly Ala Leu Glu Ala Glu Met Asp
    450                 455                 460

Gly Ala Lys Gly Arg Leu Ser Ser Gly His Leu Lys Cys Arg Leu Lys
465                 470                 475                 480

Met Asp Lys Leu Arg Leu Lys Gly Val Ser Tyr Ser Leu Cys Thr Ala
                485                 490                 495

Ala Phe Thr Phe Thr Lys Ile Pro Ala Glu Thr Leu His Gly Thr Val
            500                 505                 510

Thr Val Glu Val Gln Tyr Ala Gly Thr Asp Gly Pro Cys Lys Val Pro
        515                 520                 525

Ala Gln Met Ala Val Asp Met Gln Thr Leu Thr Pro Val Gly Arg Leu
    530                 535                 540

Ile Thr Ala Asn Pro Val Ile Thr Glu Ser Thr Glu Asn Ser Lys Met
545                 550                 555                 560

Met Leu Glu Leu Asp Pro Pro Phe Gly Asp Ser Tyr Ile Val Ile Gly
                565                 570                 575

Val Gly Glu Lys Lys Ile Thr His His Trp His Arg Ser Gly Ser Thr
            580                 585                 590

Ile Gly Lys Ala Phe Glu Ala Thr Val Arg Gly Ala Lys Arg Met Ala
        595                 600                 605

Val Leu Gly Asp Thr Ala Trp Asp Phe Gly Ser Val Gly Gly Ala Leu
    610                 615                 620

Asn Ser Leu Gly Lys Gly Ile His Gln Ile Phe Gly Ala Ala Phe Lys
625                 630                 635                 640

Ser Leu Phe Gly Gly Met Ser Trp Phe Ser Gln Ile Leu Ile Gly Thr
                645                 650                 655

Leu Leu Met Trp Leu Gly Leu Asn Thr Lys Asn Gly Ser Ile Ser Leu
            660                 665                 670

Met Cys Leu Ala Leu Gly Gly Val Leu Ile Phe Leu Ser Thr Ala Val
        675                 680                 685

Ser Ala
    690

<210> SEQ ID NO 7
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 7

Met Glu Thr Pro Ala Gln Leu Leu Phe Leu Leu Leu Leu Trp Leu Pro
1               5                   10                  15

Asp Thr Thr Gly
            20

<210> SEQ ID NO 8
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 8

```
Met Asp Trp Thr Trp Ile Leu Phe Leu Val Ala Ala Ala Thr Arg Val
1               5                   10                  15

His Ser

<210> SEQ ID NO 9
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 9

Met Leu Gly Ser Asn Ser Gly Gln Arg Val Val Phe Thr Ile Leu Leu
1               5                   10                  15

Leu Leu Val Ala Pro Ala Tyr Ser
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Met Lys Cys Leu Leu Tyr Leu Ala Phe Leu Phe Ile Gly Val Asn Cys
1               5                   10                  15

Ala

<210> SEQ ID NO 11
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 11

Met Trp Leu Val Ser Leu Ala Ile Val Thr Ala Cys Ala Gly Ala
1               5                   10                  15

<210> SEQ ID NO 12
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(3)
<223> OTHER INFORMATION: n is a or g

<400> SEQUENCE: 12 ccnccaugg                                                                9

<210> SEQ ID NO 13
<211> LENGTH: 11
<212> TYPE: RNA
<213> ORGANISM: Artificial Sequence
<220> FEATURE:
<223> OTHER INFORMATION: Synthetic Polynucleotide

<400> SEQUENCE: 13
gggauccuac c                                                            11
```

```
<210> SEQ ID NO 14
<211> LENGTH: 9
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (8)..(9)
<223> OTHER INFORMATION: n is a or u

<400> SEQUENCE: 14 uuauuuann                                                              9
```